US010391239B2

(12) United States Patent
Lorenzen et al.

(10) Patent No.: US 10,391,239 B2
(45) Date of Patent: Aug. 27, 2019

(54) RESERVOIR PRESSURE EQUALIZATION SYSTEMS AND METHODS

(71) Applicant: MEDTRONIC MINIMED, INC., Northridge, CA (US)

(72) Inventors: Eric M. Lorenzen, Granada Hills, CA (US); Edgardo Halili, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 401 days.

(21) Appl. No.: 15/423,558

(22) Filed: Feb. 2, 2017

(65) Prior Publication Data

US 2017/0143896 A1    May 25, 2017

Related U.S. Application Data

(60) Division of application No. 13/192,415, filed on Jul. 27, 2011, now Pat. No. 9,598,210, which is a
(Continued)

(51) Int. Cl.
*A61M 37/00* (2006.01)
*A61M 5/142* (2006.01)
(Continued)

(52) U.S. Cl.
CPC ...... *A61M 5/14248* (2013.01); *A61M 5/1452* (2013.01); *A61M 5/1456* (2013.01);
(Continued)

(58) Field of Classification Search
CPC .... A61B 5/14532; A61M 2005/14264; A61M 2005/14268; A61M 2039/267;
(Continued)

(56) References Cited

U.S. PATENT DOCUMENTS 4,507,118 A     3/1985 Dent
5,413,564 A     5/1995 Silver et al.
(Continued)

FOREIGN PATENT DOCUMENTS

EP           1716879 A1      11/2008
WO      WO 01/070307          9/2001
(Continued)

*Primary Examiner* — Jason E Flick
(74) *Attorney, Agent, or Firm* — Lorenz & Kopf, LLP

(57) ABSTRACT

Various embodiments of the present invention are directed to equalizing pressure in a reservoir containing fluidic media, possibly due to imperfect installation of the reservoir or an external influence such as an altitude or a temperature change. In various embodiments, fluidic media may be expelled from the reservoir through a needle and contained in an interior volume of a pierceable member before the needle pierces the pierceable member to establish a flow path to a user. In other embodiments, fluidic media may be expelled through a port of the reservoir into a chamber or to the outside environment. In further embodiments, fluidic media may be expelled through a channel in a plunger head and out a passage in the reservoir when the channel and passage are aligned. In other embodiments, fluidic media may be expelled through a valve, and the valve may be pierceable by a needle to establish a flow path to the user.

20 Claims, 23 Drawing Sheets

Related U.S. Application Data continuation-in-part of application No. 11/965,578, filed on Dec. 27, 2007, now Pat. No. 8,313,467.

(51) Int. Cl.

| | | |
|---|---|---|
| *A61M 5/145* | (2006.01) | |
| *B65D 51/16* | (2006.01) | |
| *F16K 17/02* | (2006.01) | |
| *A61M 5/172* | (2006.01) | |
| *A61B 5/145* | (2006.01) | |
| *A61M 39/26* | (2006.01) | |

(52) U.S. Cl.
CPC ....... *A61M 5/1723* (2013.01); *B65D 51/1633* (2013.01); *F16K 17/02* (2013.01); *A61B 5/14532* (2013.01); *A61M 2005/14264* (2013.01); *A61M 2005/14268* (2013.01); *A61M 2039/267* (2013.01); *A61M 2205/0216* (2013.01); *A61M 2205/18* (2013.01); *A61M 2205/3337* (2013.01); *A61M 2205/3592* (2013.01); *A61M 2205/50* (2013.01); *A61M 2205/7527* (2013.01); *A61M 2205/7536* (2013.01); *A61M 2230/201* (2013.01); *Y10T 137/0318* (2015.04); *Y10T 137/0396* (2015.04)

(58) Field of Classification Search
CPC ............ A61M 5/14248; A61M 5/1452; A61M 5/1456; B65D 51/1633; F16K 17/02; Y10T 137/0318; Y10T 137/0396
USPC ........................................................ 604/131
See application file for complete search history.

(56) References Cited

U.S. PATENT DOCUMENTS

| | | |
|---|---|---|
| 5,785,681 A | 7/1998 | Indravudh |
| 6,102,896 A | 8/2000 | Roser |
| 6,589,229 B1 | 7/2003 | Connelly et al. |
| 7,749,194 B2 | 7/2010 | Edwards et al. |
| 2001/0037087 A1 | 11/2001 | Knauer |
| 2001/0041869 A1 | 11/2001 | Causey, III et al. |
| 2003/0032940 A1* | 2/2003 | Doyle ................. A61M 39/045 604/533 |
| 2003/0125672 A1 | 7/2003 | Adair et al. |
| 2003/0144633 A1 | 7/2003 | Kirchhofer |
| 2003/0212364 A1 | 11/2003 | Mann et al. |
| 2004/0073095 A1 | 4/2004 | Causey, III et al. |
| 2005/0065760 A1 | 3/2005 | Murtfeldt et al. |
| 2005/0101939 A1* | 5/2005 | Mitchell ................ A61M 39/10 604/533 |
| 2006/0253085 A1 | 11/2006 | Geismar et al. |

FOREIGN PATENT DOCUMENTS

| | | |
|---|---|---|
| WO | WO 03/024503 A2 | 3/2003 |
| WO | WO 04/030716 | 4/2004 |
| WO | WO 04/030717 | 4/2004 |
| WO | WO 2005/002642 A2 | 1/2005 |
| WO | WO 2005/002649 A1 | 1/2005 |
| WO | WO 2006/121921 A2 | 11/2006 |

\* cited by examiner

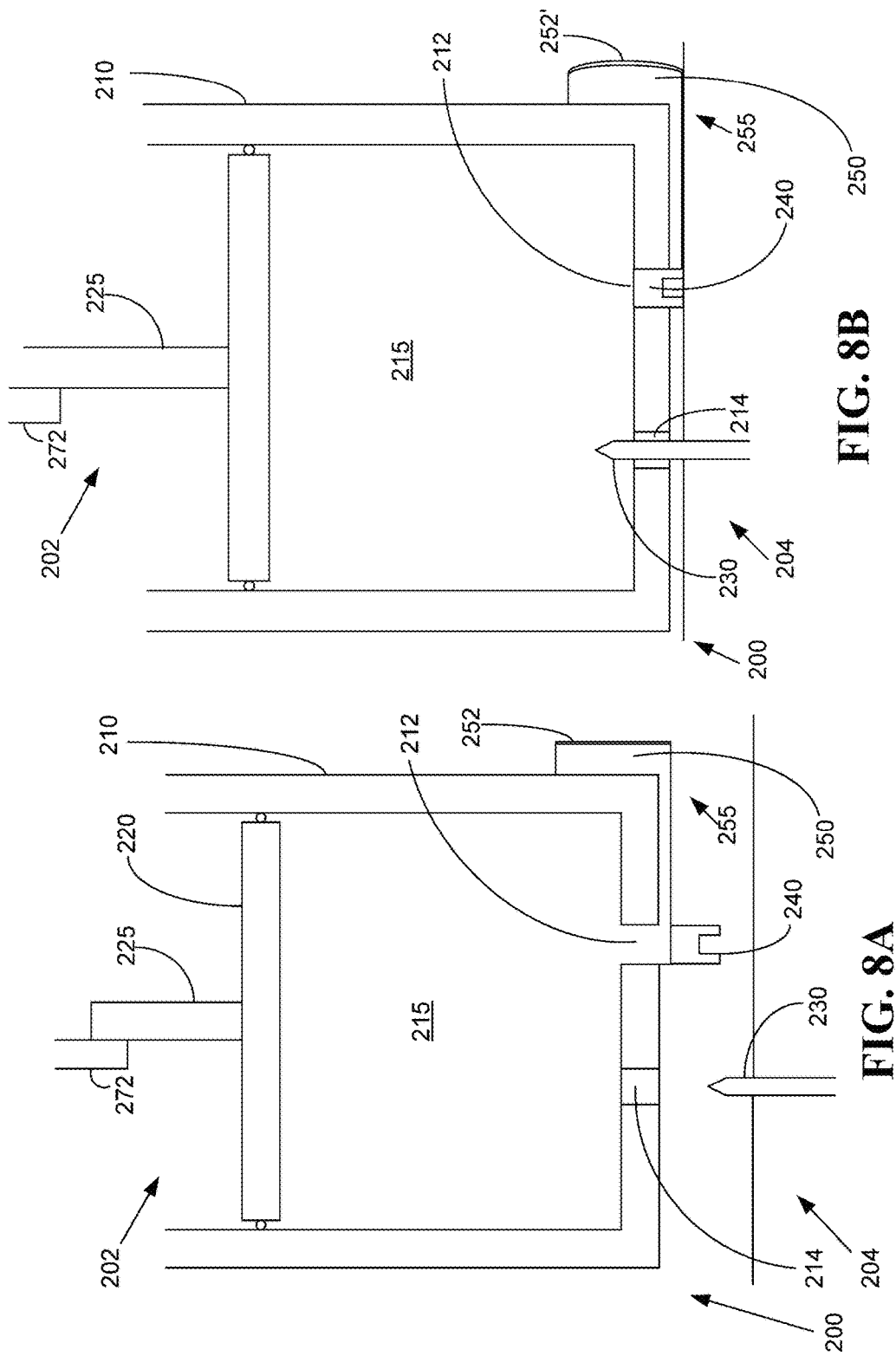

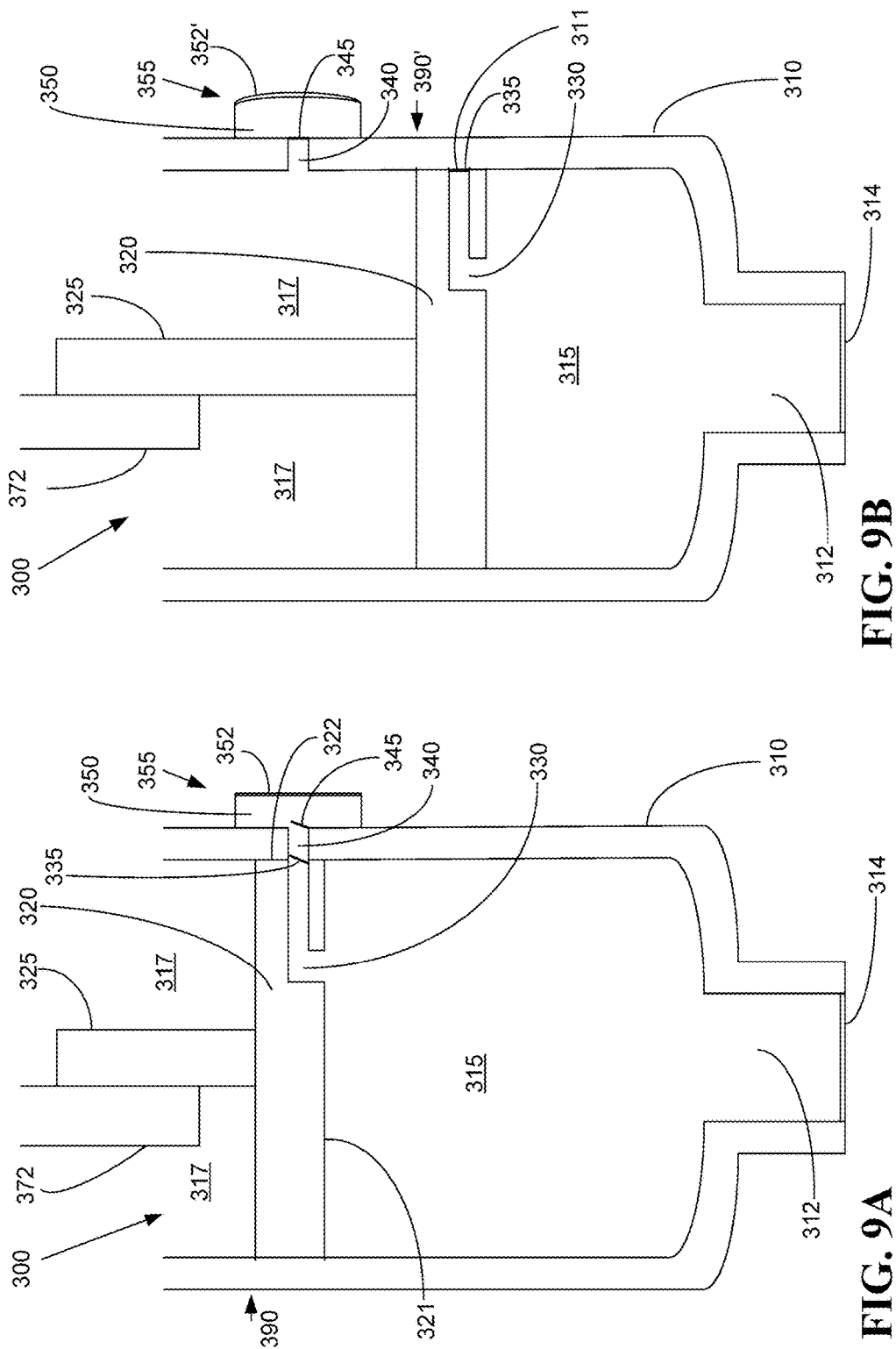

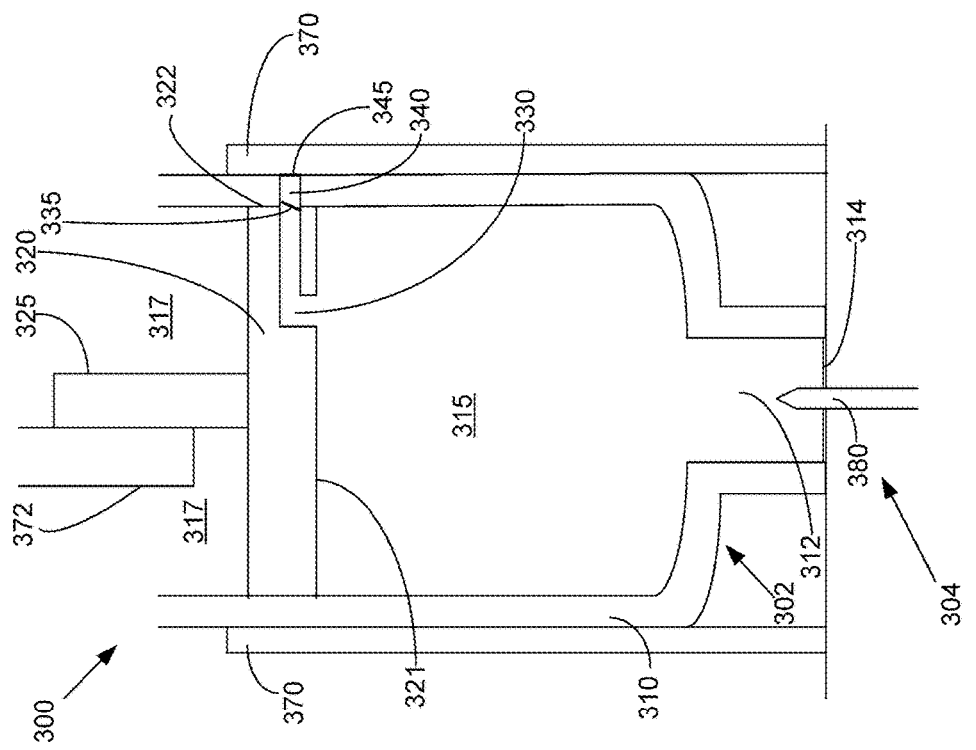

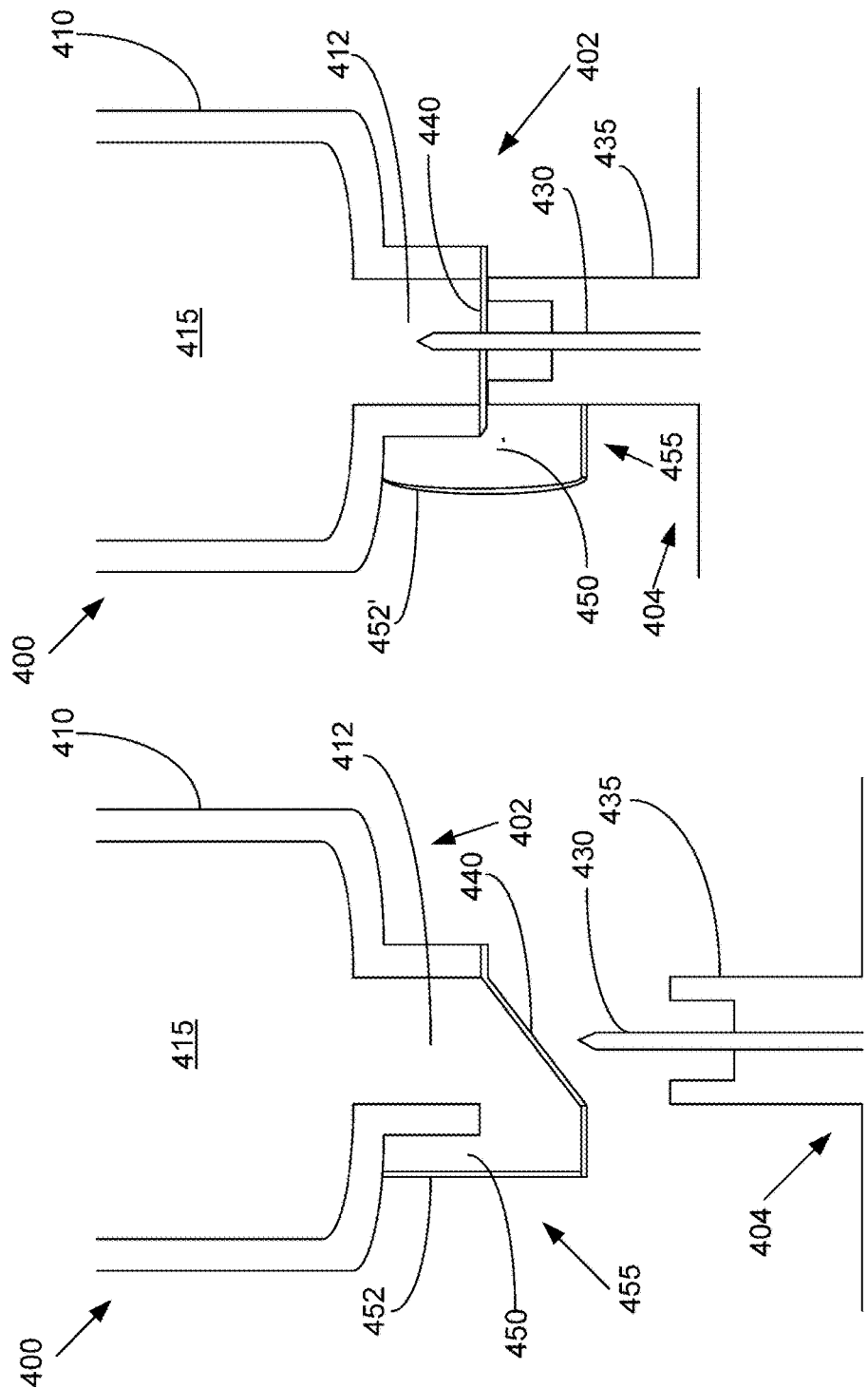

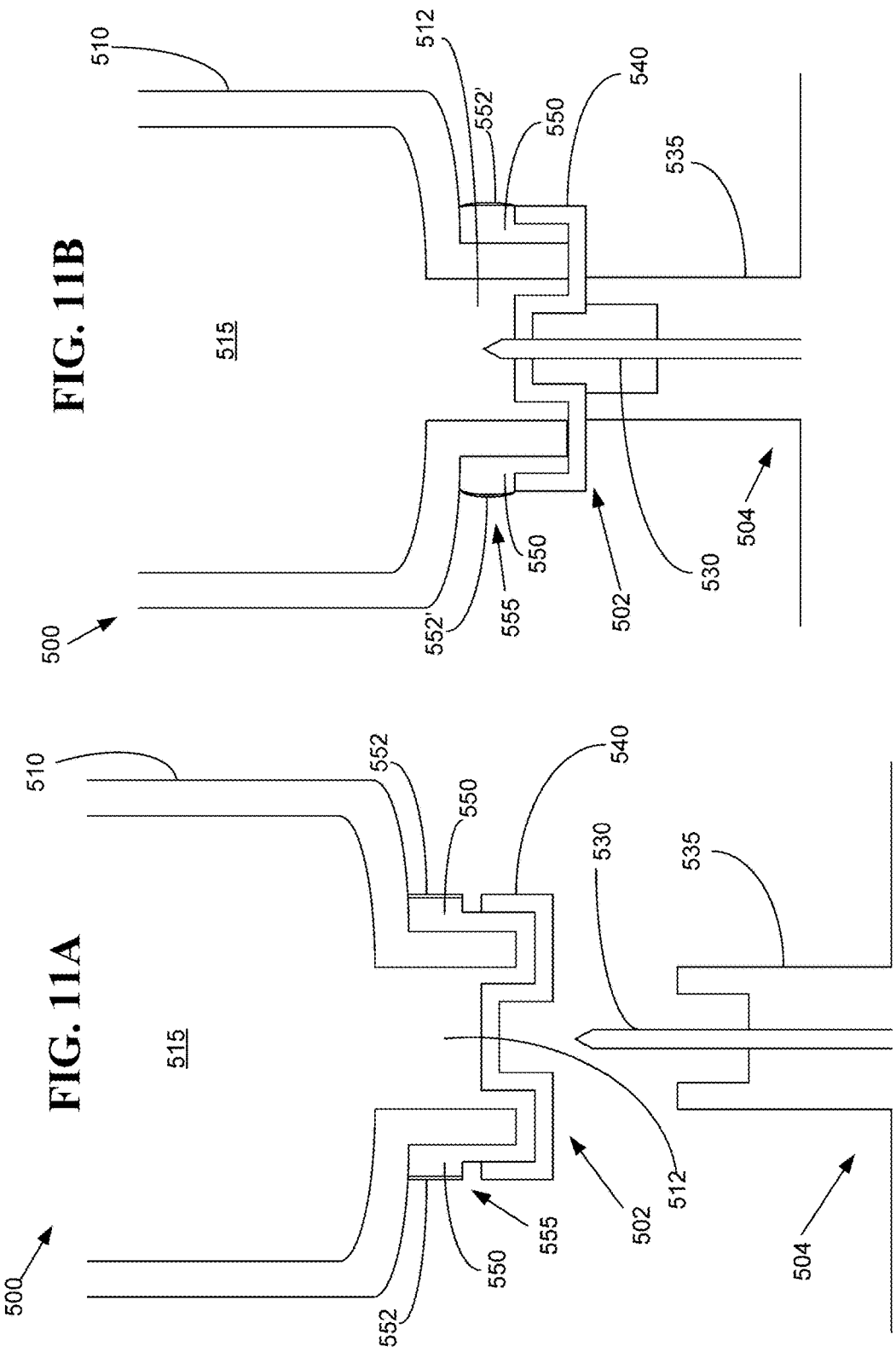

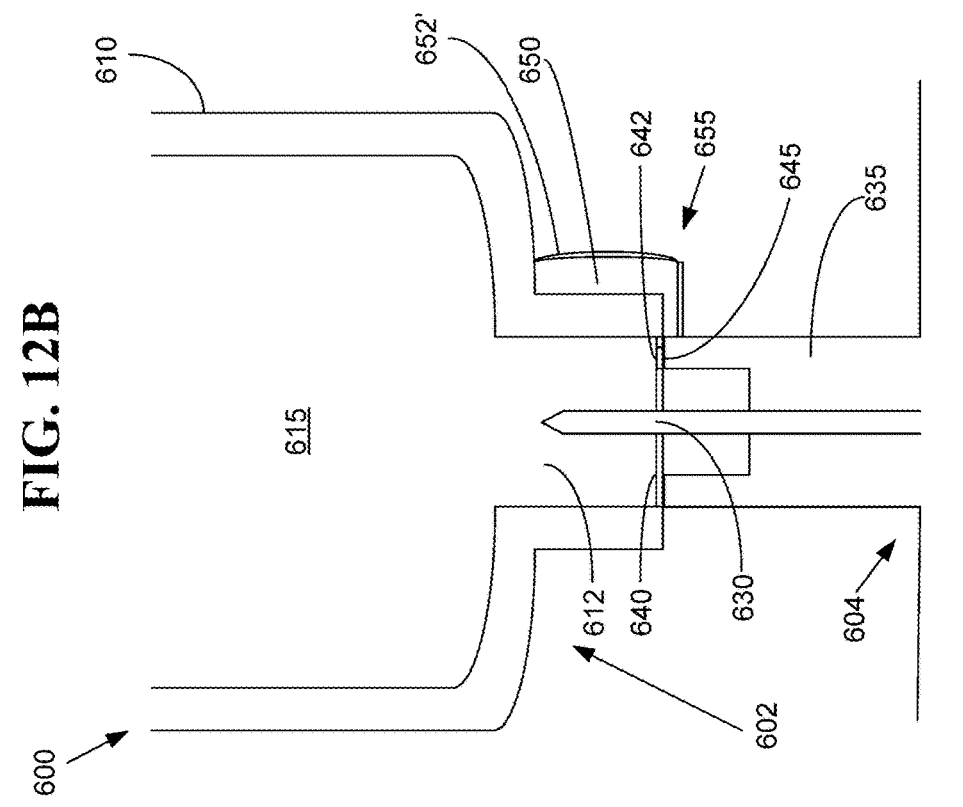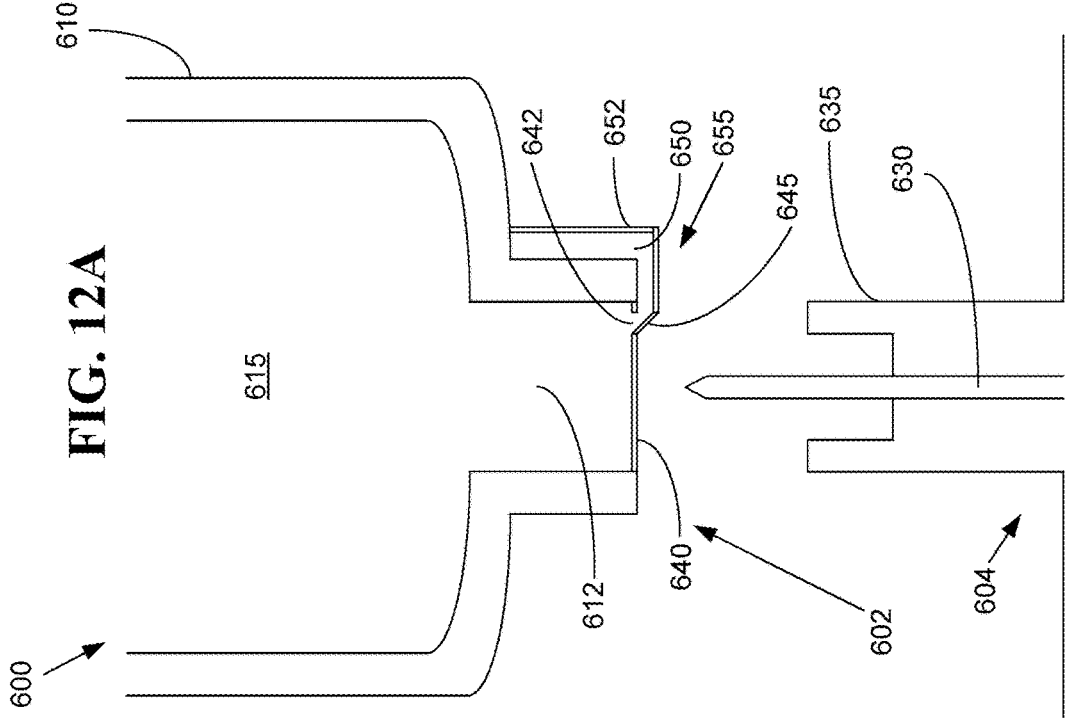

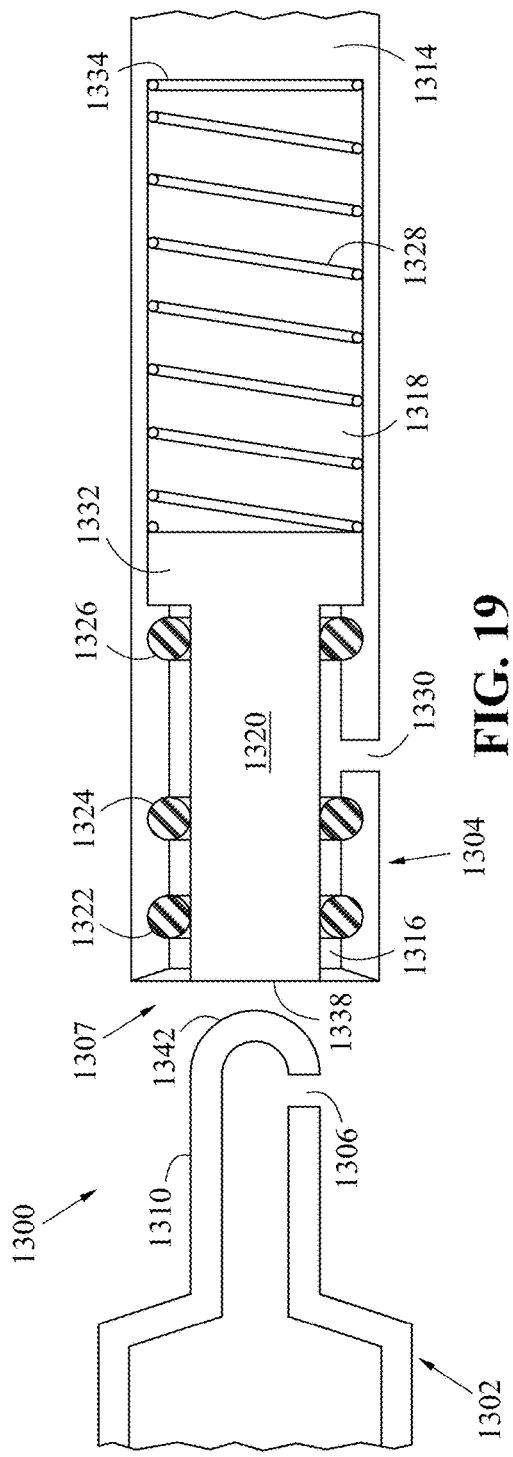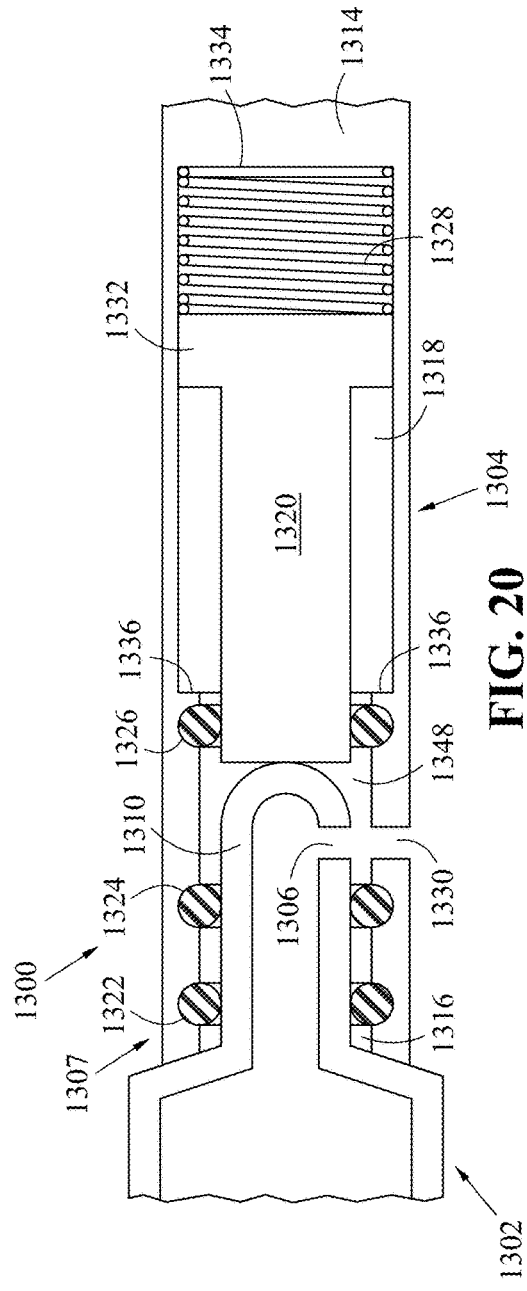

RESERVOIR PRESSURE EQUALIZATION SYSTEMS AND METHODS

CROSS-REFERENCE TO RELATED APPLICATION

This application is a divisional of U.S. patent application Ser. No. 13/192,415, filed Jul. 27, 2011 and published as United States patent application publication number US 2011/0282282 A1, which was a continuation-in-part of U.S. patent application Ser. No. 11/965,578, filed Dec. 27, 2007 and published as United States patent application publication number US 2009/0171324 A1.

TECHNICAL FIELD

Embodiments of the present invention relate generally to systems and methods with reservoirs and, in specific embodiments, to systems and methods allowing for pressure equalization of fluidic media contained within the reservoirs.

BACKGROUND

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may contain reservoirs of fluidic media, such as, but is not limited to, insulin. External pump type delivery devices may be connected in fluid flow communication to a patient or user, for example, through a suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that doses of insulin may be calculated and delivered automatically to a patient at any time during the day or night. Furthermore, when used in conjunction with glucose sensors or monitors, insulin pumps may be automatically controlled to provide appropriate doses of fluidic media at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

However, one of the problems with pump type delivery devices is that a bolus of fluidic media could be delivered inadvertently to the patient in a case where the reservoir of fluidic media is pressurized. FIG. 13 illustrates a conventional reservoir system 700. The reservoir system 700 may include a reservoir 710 with an interior volume 715 filled with fluidic media, a plunger head 720, a plunger shaft 725, and a driveshaft 772 mechanically connected to a drive motor 774. The reservoir 710 may include a self-sealing septum 711. When the reservoir 710 is inserted in the reservoir system 700, the plunger shaft 725 mechanically couples with the driveshaft 772 by use of complementing mating parts, such as threads, for example. If the complementing threads of the plunger shaft 725 and the driveshaft 772 are not perfectly aligned, the plunger shaft 725 shifts a small distance, such as a half thread forward or backward, so that the threads can align and couple together. Accordingly, the plunger head 720, which is connected to the plunger shaft 725, is moved a half thread forward or backward within the reservoir 710. If the plunger head 720 is moved forward, pressure in the interior volume 715 of the reservoir 710 is increased. As a result, this could cause the reservoir system 700 inadvertently to pump a small bolus of fluidic media to a user once a fluid path between the reservoir system 700 and the user is established. Alternatively, the interior volume 715 of the reservoir 710 could become pressurized due to a change in an external influence such as an altitude or a temperature as well, which could also lead to an inadvertent bolus of fluid being delivered to the user once the fluid path between the reservoir system 700 and the user is established. The opposite effect is true for a system that draws the plunger head backwards, establishing a negative pressure in the reservoir. In this case, bodily fluids may be drawn into the fluid path or reservoir when the fluid system is fully connected.

BRIEF SUMMARY

Various embodiments of the present invention are directed to equalizing pressure in a reservoir containing fluidic media. This may prevent patients from inadvertently receiving boluses of fluidic media because of increased pressure within a reservoir of a medical device due to, for example, imperfect alignment of a plunger shaft and a driveshaft within the medical device, or a change in an external influence, such as an altitude or a temperature change. Additionally, it may prevent the system from drawing bodily fluids into the reservoir if the reservoir is biased with a negative pressure.

A system for equalizing pressure in a reservoir in accordance with an embodiment of the present invention may include, but is not limited to, a structure, a needle, and a pierceable member. The structure may have a chamber. The needle may be connectable to the reservoir for allowing fluidic media contained in the reservoir to flow through the needle when the needle is connected to the reservoir. The pierceable member may be moveable within the chamber and pierceable by the needle. The pierceable member may have an interior volume for containing fluidic media expelled from the reservoir before the pierceable member is pierced by the needle. In some embodiments, the interior volume of the pierceable member may allow for containing fluidic media that flows through the needle from the reservoir before the pierceable member is pierced by the needle. Fluidic media may be expelled from the reservoir in a case where a pressure difference exists between the reservoir and the chamber. In some embodiments, fluidic media may be expelled from the reservoir in a case where a pressure difference exists between the reservoir and the interior volume of the pierceable member. An end of the needle may be located at least substantially within the interior volume of the pierceable member before the pierceable member is pierced by the needle. A cross-section of the pierceable member may be U-shaped.

The system may further include a first housing portion and a second housing portion. The first housing portion may be adapted to be carried by a user. The second housing portion may be configured to be selectively operatively engaged with and disengaged from the first housing portion. The structure may be supported by one of the first and second housing portions. The pierceable member may be positioned to be pierced by the needle when the first housing portion and the second housing portion are operatively engaged. The needle may be positioned to enter the other of the first and second housing portions from the one of the first and second housing portions when the first housing portion and the second housing portion are operatively engaged.

The pierceable member may have a first end and a second end. The first end may be for contacting the other of the first and second housing portions from the one of the first and second housing portions when the first housing portion and the second housing portion are operatively engaged. The second end may be located on an opposite side of the pierceable member from the first end.

The chamber may have a first portion and a second portion. The first portion of the chamber may be adjacent to the second end of the pierceable member. The first portion of the chamber may be for containing fluidic media in a case where fluidic media flows out of the interior volume of the pierceable member. The first portion of the chamber may be located between the pierceable member and the reservoir. The second portion of the chamber may be adjacent to an opposite side of the pierceable member from the first portion of the chamber. The second portion of the chamber may be for containing fluidic media in a case where fluidic media flows out of the first portion of the chamber. The pierceable member may further include a seal member. The structure may have an opening that communicates with the chamber. The opening may allow for fluidic media to be purged from the chamber in a case where fluidic media flows out of the interior volume of the pierceable member.

The system may further include a bias member. The bias member may be arranged to impart a bias force on the pierceable member. The bias member may be a spring. In other embodiments, the pierceable member may have a resiliently flexible portion. The resiliently flexible portion may be for providing a bias force on the pierceable member to maintain the pierceable member within the chamber. In various embodiments, the needle may have a longitudinal dimension and a central axis along the longitudinal dimension. The interior volume of the pierceable member may be curved concavely relative to the central axis of the needle. In various embodiments, at least one seal member may be positioned between the structure and the pierceable member.

A method for equalizing a pressure within a reservoir may include, but is not limited to, providing a structure having a chamber, locating a needle connectable to the reservoir for allowing fluidic media contained in the reservoir to flow through the needle when the needle is connected to the reservoir, and locating a pierceable member moveable within the chamber, where the pierceable member is pierceable by the needle, and where the pierceable member has an interior volume for containing fluidic media expelled from the reservoir before the pierceable member is pierced by the needle.

In an embodiment of a system for equalizing pressure, the system may include, but is not limited to, a reservoir, a plug, and a structure. The reservoir may have a port and an interior volume for containing fluidic media. The plug may be positioned relatively offset to the port of the reservoir. The plug may be for closing the port of the reservoir when the plug is in a closed position. The plug may comprise one of a flapper valve and a disc valve. The structure may have a chamber in flow communication with the interior volume of the reservoir. The chamber may allow for collecting fluidic media expelled from the interior volume of the reservoir through the port in a case where a pressure difference exists between the interior volume of the reservoir and the chamber before the plug is held in the closed position.

The system may further include a first housing portion and a second housing portion. The first housing portion may be adapted to be carried by a user. The second housing portion may be configured to be selectively operatively engaged with and disengaged from the first housing portion. The reservoir may be supported by one of the first and second housing portions. The plug may be positioned to close the port of the reservoir when the first housing portion and the second housing portion are operatively engaged. The other of the first and second housing portions from the one of the first and second housing portions may have a first surface for moving and holding the plug in the closed position when the first housing portion and the second housing portion are operatively engaged.

The system may further include a needle. The needle may be supported by the other of the first and second housing portions from the one of the first and second housing portions. The needle may be for piercing a portion of the reservoir and entering the interior volume of the reservoir when the first housing portion and the second housing portion are operatively engaged. The needle may allow for fluidic media contained in the interior volume of the reservoir to flow through the needle when the needle is in the interior volume of the reservoir. In some embodiments, the portion of the reservoir pierced by the needle when the first housing portion and the second housing portion are operatively engaged may be the plug.

The system may further include a membrane configured to expand to increase the volume of the chamber in a case where the chamber sufficiently fills with fluidic media. The membrane may be an elastomeric membrane. The system may include one of a hydrophobic filter and a hydrophilic filter. The chamber may be located within the reservoir. In some embodiments, the chamber may be located outside of the reservoir. The structure may have an opening that communicates with the chamber, where the opening may allow for fluidic media to be purged from the chamber.

A method for equalizing pressure may include, but is not limited to, providing a reservoir having a port and an interior volume for containing fluidic media, locating a plug positioned relatively offset to the port of the reservoir, where the plug allows for closing the port of the reservoir when the plug is in a closed position, and locating a structure having a chamber in flow communication with the interior volume of the reservoir, where the chamber allows for collecting fluidic media expelled from the interior volume of the reservoir from the port in a case where a pressure difference exists between the interior volume of the reservoir and the chamber before the plug is held in the closed position.

In an embodiment of a system for equalizing pressure, the system may include, but is not limited to, a reservoir and a plunger head. The reservoir may have a passage and an interior volume for containing fluidic media. The plunger head may have a first surface and a second surface. The plunger head may have a channel connecting the first surface and the second surface. The plunger head may be moveable within the reservoir to align the channel in the plunger head and the passage in the reservoir. When the channel in the plunger head and the passage in the reservoir are aligned and a pressure difference exists between the interior volume of the reservoir and the passage, fluidic media may be expelled from the interior volume of the reservoir through the passage.

In various embodiments, the interior volume allows for containing fluidic media. In some embodiments, the reservoir may have a second interior volume. The plunger head may be located between the interior volume of the reservoir and the second interior volume of the reservoir. The first surface of the plunger head may be in contact with fluidic media when fluidic media is in the interior volume of the reservoir.

In various embodiments, the passage in the reservoir and the channel in the plunger head may be aligned at a first position of the plunger head in the reservoir. The plunger head may be advanceable from the first position to a second position. The passage in the reservoir and the channel in the plunger head may be disaligned when the plunger head is in the second position.

In various embodiments, the system may further include a first housing portion and a second housing portion. The first housing portion may be adapted to be carried by a user. The second housing portion may be configured to be selectively operatively engaged with and disengaged from the first housing portion. The reservoir may be supported by one of the first and second housing portions.

In various embodiments, the system may further include a mating piece. The mating piece may be supported by the other of the first and second housing portions from the one of the first and second housing portions. The mating piece may be for closing the passage when the first housing portion and the second housing portion are operatively engaged. The system may also include a needle. The needle may be supported by the other of the first and second housing portions from the one of the first and second housing portions. The needle may be for piercing the reservoir and entering the interior volume of the reservoir when the first housing portion and the second housing portion are operatively engaged. The needle may be for allowing fluidic media contained in the interior volume of the reservoir to flow through the needle when the needle is in the interior volume of the reservoir. The plunger head may be advanceable in the reservoir from the first position to the second position before the first housing portion and the second housing portion are operatively engaged. The first surface of the plunger head and the second surface of the plunger head may be perpendicular to each other.

In various embodiments, the system may further include a valve positioned relative to an end of the channel in the plunger head. The valve may allow for closing the channel in the plunger head when the valve is in a closed position. In some embodiments, the system may include a valve positioned relative to an end of the passage in the reservoir. The valve may allow for closing the passage in the reservoir when the valve is in a closed position.

In various embodiments, the system may further include a structure. The structure may have a chamber connected to the passage. The chamber may allow for collecting fluidic media that flows through the passage in the reservoir. Fluidic media may flow through the passage when the channel in the plunger head and the passage in the reservoir are aligned and a pressure difference exists between the interior volume of the reservoir and the passage. The structure may include a membrane configured to expand to increase the volume of the chamber in a case where the chamber sufficiently fills with fluidic media. The membrane may comprise an elastomeric membrane. The system may include one of a hydrophobic filter and a hydrophilic filter. The chamber may be located within the reservoir. In some embodiments, the chamber may be located outside of the reservoir. The system may further include at least one seal member positioned between the plunger head and the reservoir.

A method for equalizing pressure may include, but is not limited to, providing a reservoir having a passage and an interior volume for containing fluidic media, and locating a plunger head having a first surface and a second surface, where the plunger head has a channel connecting the first surface and the second surface, the plunger head is moveable within the reservoir to align the channel in the plunger head and the passage in the reservoir, and when the channel in the plunger head and the passage in the reservoir are aligned and a pressure difference exists between the interior volume of the reservoir and the passage, fluidic media is expelled from the interior volume of the reservoir through the passage.

A system for equalizing pressure may include, but is not limited to, a mating piece, a needle, a reservoir, and at least one valve. The needle may be supported by the mating piece. The reservoir may have an interior volume for containing fluidic media. The mating piece may be configured to be selectively operatively engaged with and disengaged from the reservoir. The reservoir may have a port for allowing fluidic media to be expelled from the interior volume of the reservoir before the reservoir and the mating piece are operatively engaged. The at least one valve may be positioned relative to an end of the port. The at least one valve may be for closing the port when the mating piece and the reservoir are operatively engaged. The needle may be for piercing the at least one valve and entering the interior volume of the reservoir when the reservoir and the mating piece are operatively engaged. The needle may allow for fluidic media contained in the interior volume of the reservoir to flow through the needle when the needle is in the interior volume of the reservoir.

In various embodiments, the system may further include a structure having a chamber connected to the port of the reservoir. The chamber may allow for collecting fluidic media expelled from the interior volume of the reservoir before the reservoir and the mating piece are operatively engaged. Fluidic media may be expelled from the interior volume of the reservoir before the reservoir and the mating piece are operatively engaged in a case where a pressure difference exists between the reservoir and the chamber. The system may further include a membrane configured to expand to increase the volume of the chamber in a case where the chamber sufficiently fills with fluidic media. The membrane may comprise an elastomeric membrane. The system may include one of a hydrophobic filter and a hydrophilic filter.

In various embodiments, the system may further include a first housing portion and a second housing portion. The first housing portion may be adapted to be carried by a user. The second housing portion may be configured to be selectively operatively engaged with and disengaged from the first housing portion. The reservoir may be supported by one of the first and second housing portions. The mating piece may be supported by the other of the first and second housing portions from the one of the first and second housing portions. The mating piece and the reservoir may be operatively engaged when the first housing portion and the second housing portion are operatively engaged.

In various embodiments, the at least one valve may have a moveable portion. The moveable portion may be moveable between an open position and a closed position such that the at least one valve is moveable by the mating piece from the open position to the closed position to close the port of the reservoir when the reservoir and the mating piece are operatively engaged. In some embodiments, the moveable portion of the at least one valve may be pierceable by the needle when the reservoir and the mating piece are operatively engaged.

In various embodiments, the at least one valve may be arranged to be held closed by the mating piece to close the port of the reservoir when the reservoir and the mating piece are operatively engaged. In some embodiments, the at least one valve may comprise one of a flapper valve and a loose fitting cap. In other embodiments, the at least one valve may comprise a covering that seals the port of the reservoir. The covering may have an opening. The opening may be for allowing fluidic media to be expelled from the interior volume of the reservoir before the reservoir and the mating piece are operatively engaged. The covering may have a second valve positioned relative to an end of the opening in the covering. The second valve may be arranged to be held closed by the mating piece to close the opening in the covering when the reservoir and the mating piece are operatively engaged. In other embodiments, the needle may be positioned to enter the opening when the reservoir and the mating piece are operatively engaged.

A method for equalizing pressure may include, but is not limited to, providing a mating piece, locating a needle supported by the mating piece, locating a reservoir having an interior volume for containing fluidic media, where the mating piece is configured to be selectively operatively engaged with and disengaged from the reservoir, and the reservoir has a port for allowing fluidic media to be expelled from the interior volume of the reservoir before the reservoir and the mating piece are operatively engaged, and locating at least one valve relative to an end of the port, where the at least one valve allows for closing the port when the mating piece and the reservoir are operatively engaged. The needle allows for piercing the at least one valve and entering the interior volume of the reservoir when the reservoir and the mating piece are operatively engaged. The needle allows for fluidic media contained in the interior volume of the reservoir to flow through the needle when the needle is in the interior volume of the reservoir.

An exemplary embodiment of a fluid delivery system presented here includes a fluid reservoir and a base assembly for the fluid reservoir. The fluid reservoir has a body section, a neck section protruding from the body section, and a fluid vent formed in the neck section to accommodate expulsion of pressurized fluidic media from the fluid reservoir. The base assembly has a sealing receptacle to receive the neck section of the fluid reservoir, the sealing receptacle forming a chamber in fluid communication with the fluid vent when the neck section is inserted into the sealing receptacle.

Another embodiment of a fluid delivery system is also provided. The fluid delivery system includes a base assembly to mate with a fluid reservoir having a neck section and a fluid vent formed in the neck section to accommodate expulsion of pressurized fluidic media from the fluid reservoir. The base assembly has a receptacle that receives and forms a seal around the neck section, and a fluid conduit to establish fluid communication with the fluid vent when the neck section is received in the receptacle.

Another exemplary embodiment of a fluid delivery system includes a fluid reservoir that cooperates with a base assembly. The fluid reservoir has a neck section and a fluid vent formed in the neck section to accommodate expulsion of pressurized fluidic media from the fluid reservoir. The base assembly has a sealing receptacle to receive the neck section. The sealing receptacle includes: a fluid delivery port; a valve to cooperate with the fluid delivery port; a recess to accommodate the neck section in an inserted state during which the neck section is received in the sealing receptacle, and to accommodate the valve in a released state during which the neck section is removed from the sealing receptacle; and a sealing arrangement to form a fluid tight seal with the neck section in the inserted state, and to form a fluid tight seal with the valve in the released state. In the inserted state, the fluid vent fluidly communicates with the fluid delivery port. In the released state, the valve cooperates with the sealing arrangement to inhibit access to the fluid delivery port.

Also provided is an exemplary embodiment of a base assembly for a fluid delivery system. The system includes a fluid reservoir with a fluid vent for expelling pressurized fluidic media from the fluid reservoir. The base assembly includes a proximal portion and a distal portion formed with a fluid delivery port to accommodate transfer of fluidic media. The base assembly further includes a valve to cooperate with the fluid delivery port. Also, the base assembly includes a recess to accommodate the fluid reservoir in a first state of the base assembly, and to accommodate the valve in a second state of the base assembly. The base assembly includes a sealing arrangement that cooperates with the valve and the fluid reservoir. In the first state, the sealing arrangement cooperates with the fluid reservoir to form a fluid tight chamber in fluid communication with the fluid vent of the fluid reservoir. In the second state, the sealing arrangement cooperates with the valve to inhibit access to the fluid delivery port.

An exemplary base assembly for a fluid delivery system comprising a fluid reservoir with a fluid vent for expelling pressurized fluidic media from the fluid reservoir includes a proximal portion and a distal portion formed with a fluid delivery port to accommodate transfer of fluidic media. The base assembly includes a valve to cooperate with the fluid delivery port. The base assembly further includes a recess to accommodate the fluid reservoir in a first state of the base assembly, and to accommodate the valve in a second state of the base assembly. Also, the base assembly includes a sealing arrangement that cooperates with the valve and the fluid reservoir.

In another embodiment, a base assembly for a fluid delivery system comprising a fluid reservoir with a fluid vent for expelling pressurized fluidic media from the fluid reservoir includes a proximal portion, a distal portion, and an intermediate portion between the proximal portion and the distal portion. The base assembly includes a fluid delivery port in the intermediate portion. The base assembly further includes a valve movable between an extended position and a retracted position, wherein the valve is located in the proximal portion, the intermediate portion, and the distal portion when in the extended position, and wherein the valve is removed from the intermediate portion and distal portion when in the retracted position. The base assembly also includes a recess to accommodate the fluid reservoir in a first state of the base assembly, and to accommodate the valve in a second state of the base assembly. The base assembly includes a sealing arrangement that cooperates with the valve and the fluid reservoir.

BRIEF DESCRIPTION OF THE DRAWINGS

FIG. 8A illustrates a cross-sectional view of a system for equalizing pressure in a first position in accordance with an embodiment of the present invention;

FIG. 8B illustrates a cross-sectional view of a system for equalizing pressure in a second position in accordance with an embodiment of the present invention;

FIG. 9A illustrates a cross-sectional view of a system for equalizing pressure in accordance with an embodiment of the present invention;

FIG. 9B illustrates a cross-sectional view of a system for equalizing pressure in accordance with an embodiment of the present invention;

FIG. 9D illustrates a cross-sectional view of a system for equalizing pressure in accordance with an embodiment of the present invention;

FIG. 10A illustrates a cross-sectional view of a system for equalizing pressure in a first position in accordance with an embodiment of the present invention;

FIG. 10B illustrates a cross-sectional view of a system for equalizing pressure in a second position in accordance with an embodiment of the present invention;

FIG. 11A illustrates a cross-sectional view of a system for equalizing pressure in a first position in accordance with an embodiment of the present invention;

FIG. 11B illustrates a cross-sectional view of a system for equalizing pressure in a second position in accordance with an embodiment of the present invention;

FIG. 12A illustrates a cross-sectional view of a system for equalizing pressure in a first position in accordance with an embodiment of the present invention;

FIG. 12B illustrates a cross-sectional view of a system for equalizing pressure in a second position in accordance with an embodiment of the present invention;

FIG. 19 illustrates a cross-sectional view of another embodiment of a needleless fluid delivery system having a vented fluid reservoir and a base assembly that seals a fluid vent of the reservoir; and FIG. 20 illustrates a cross-sectional view of the needleless fluid delivery system shown in FIG. 19, with the fluid reservoir coupled to the base assembly.

DETAILED DESCRIPTION

Figure 1:
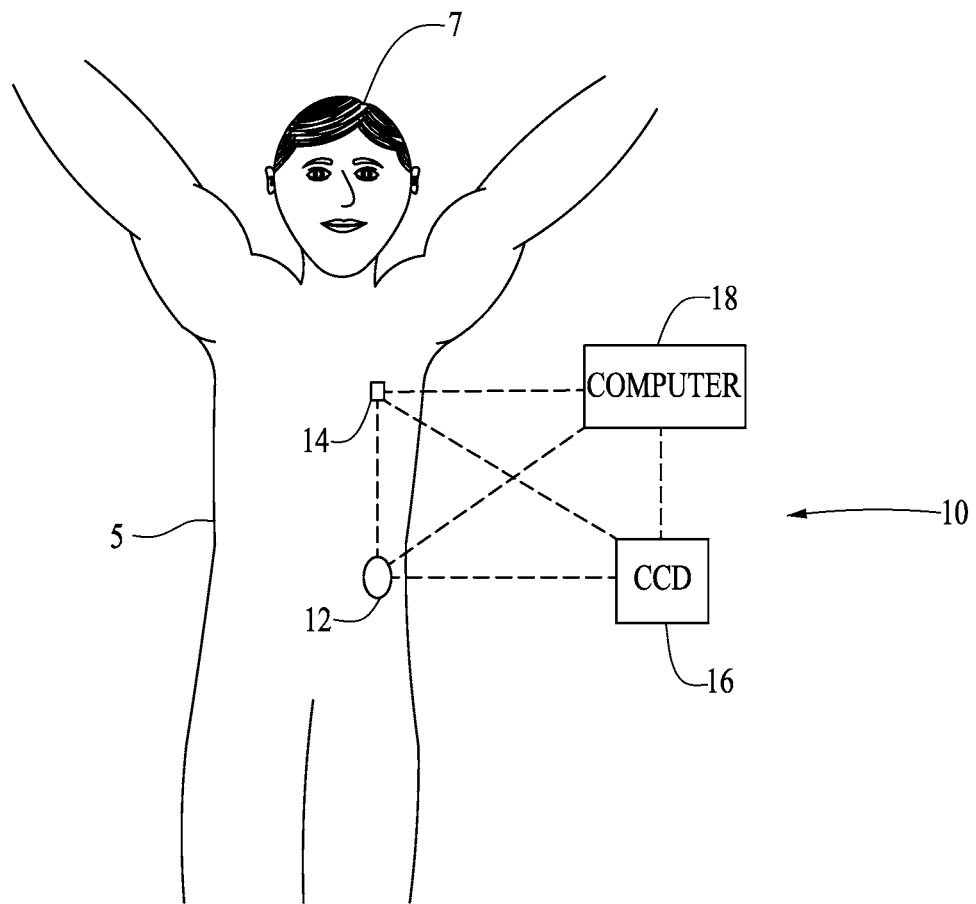
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user 7. The locations at which the delivery device 12 and the sensing device 14 are secured to the body 5 of the user 7 in FIG. 1 are provided only as representative, non-limiting, examples.

The delivery device 12 is configured to deliver fluidic media to the body 5 of the user 7. In various embodiments, fluidic media includes a liquid, a fluid, a gel, or the like. In some embodiments, fluidic media includes a medicine or a drug for treating a disease or a medical condition. For example, fluidic media may include insulin for treating diabetes, or may include a drug for treating pain, cancer, a pulmonary disorder, HIV, or the like. In some embodiments, fluidic media includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user 7. For example, the sensing device 14 may include electronics and enzymes reactive to a biological condition, such as a blood glucose level, or the like, of the user 7. In various embodiments, the sensing device 14 may be secured to the body 5 of the user 7 or embedded in the body 5 of the user 7 at a location that is remote from the location at which the delivery device 12 is secured to the body 5 of the user 7. In various other embodiments, the sensing device 14 may be incorporated within the delivery device 12.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18. Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
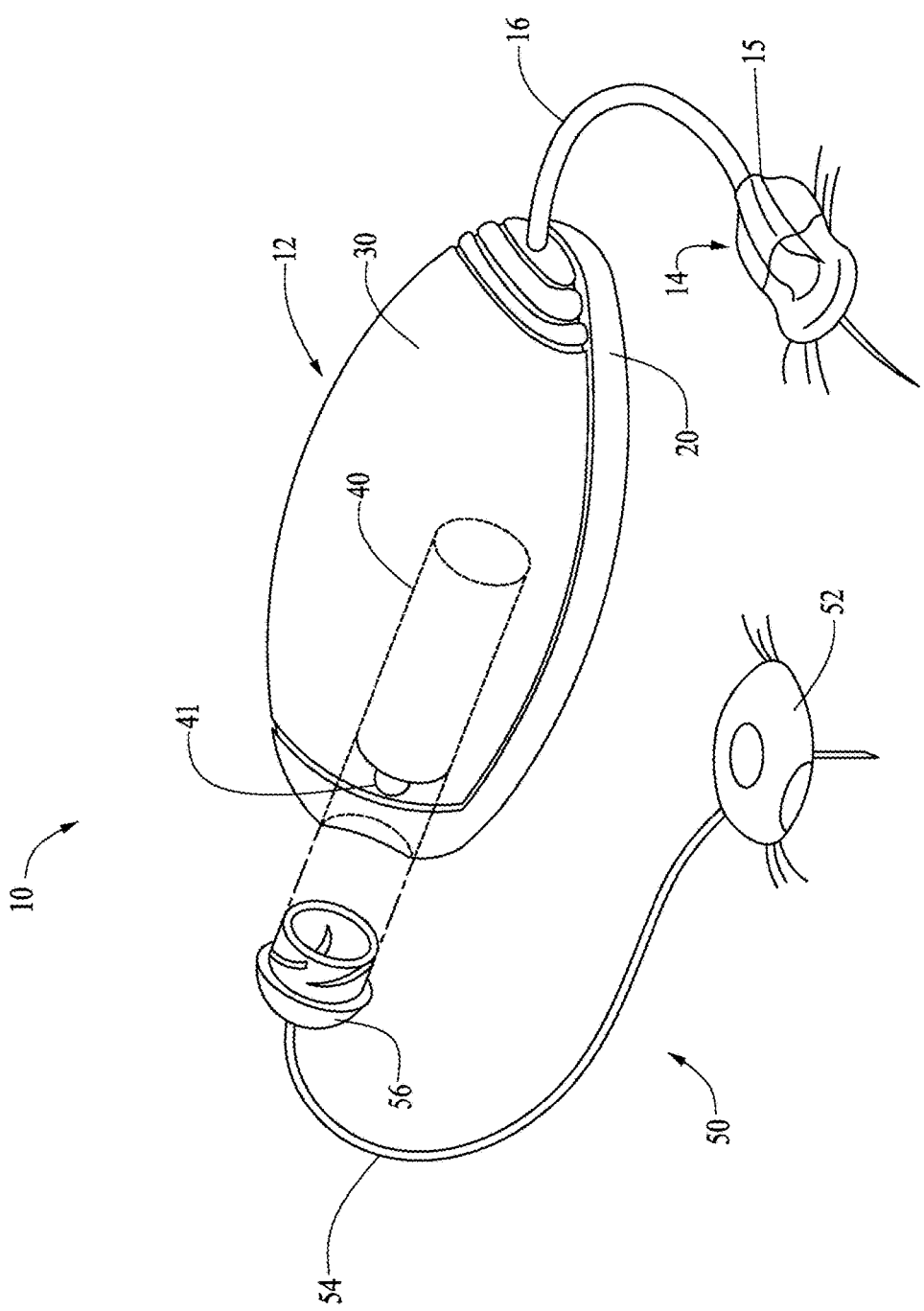
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir 40. The delivery device 12 may further include an infusion path 50.

Elements of the delivery device 12 that ordinarily contact the body of a user or that ordinarily contact fluidic media during operation of the delivery device 12 may be considered as a disposable portion of the delivery device 12. For example, a disposable portion of the delivery device 12 may include the disposable housing 20 and the reservoir 40. The disposable portion of the delivery device 12 may be recommended for disposal after a specified number of uses.

On the other hand, elements of the delivery device 12 that do not ordinarily contact the body of the user or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user or fluidic media during normal operation of the delivery device 12 and, thus, may be retained for re-use with replaced disposable portions of the delivery device 12.

In various embodiments, the disposable housing 20 supports the reservoir 40 and has a bottom surface (facing downward and into the page in FIG. 2) that is configured to secure to the body of a user. An adhesive may be employed at an interface between the bottom surface of the disposable housing 20 and the skin of a user, so as to adhere the disposable housing 20 to the skin of the user. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the skin of the user.

The reservoir 40 is configured for containing or holding fluidic media, such as, but not limited to insulin. In various embodiments, the reservoir 40 includes a hollow interior volume for receiving fluidic media, such as, but not limited to, a cylinder-shaped volume, a tubular-shaped volume, or the like. In some embodiments, the reservoir 40 may be provided as a cartridge or canister for containing fluidic media. In various embodiments, the reservoir 40 is able to be refilled with fluidic media. In further embodiments, the reservoir 40 is pre-filled with fluidic media.

The reservoir 40 may be supported by the disposable housing 20 in any suitable manner. For example, the disposable housing 20 may be provided with projections or struts (not shown), or a trough feature (not shown), for holding the reservoir 40. In some embodiments, the reservoir 40 may be supported by the disposable housing 20 in a manner that allows the reservoir 40 to be removed from the disposable housing 20 and replaced with another reservoir. Alternatively, or in addition, the reservoir 40 may be secured to the disposable housing 20 by a suitable adhesive, a strap, or other coupling structure.

In various embodiments, the reservoir 40 includes a port 41 for allowing fluidic media to flow into and/or flow out of the interior volume of the reservoir 40. In some embodiments, the infusion path 50 includes a connector 56, a tube 54, and a needle apparatus 52. The connector 56 of the infusion path 50 may be connectable to the port 41 of the reservoir 40. In various embodiments, the disposable housing 20 is configured with an opening near the port 41 of the reservoir 40 for allowing the connector 56 of the infusion path 50 to be selectively connected to and disconnected from the port 41 of the reservoir 40.

In various embodiments, the port 41 of the reservoir 40 is covered with or supports a septum (not shown in FIG. 2), such as a self-sealing septum, or the like. The septum may be configured to prevent fluidic media from flowing out of the reservoir 40 through the port 41 when the septum is not pierced. Also, in various embodiments, the connector 56 of the infusion path 50 includes a needle for piercing the septum covering the port 41 of the reservoir 40 so as to allow fluidic media to flow out of the interior volume of the reservoir 40. Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user. Also, in various embodiments, the tube 54 connects the connector 56 with the needle apparatus 52 and is hollow, such that the infusion path 50 is able to provide a path to allow for the delivery of fluidic media from the reservoir 40 to the body of a user.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts. In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir 40 to force fluidic media out of the reservoir 40 and into an infusion path, such as the infusion path 50, for delivery to a user. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir 40 and to drive the plunger head in a direction to force fluidic media out of the port 41 of the reservoir 40 and to the user. Also, in some embodiments, the motor may be controllable to reverse direction so as to move the plunger arm and the plunger head to cause fluid to be drawn into the reservoir 40 from a patient. The motor may be arranged within the durable housing 30 and the reservoir 40 may be correspondingly arranged on the disposable housing 20, such that the operable engagement of the motor with the plunger head, through the appropriate linkage, occurs automatically upon the user connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user, a greater level of user comfort may be achieved when the disposable housing 20 is secured to the skin of the user. Also, a flexible disposable housing 20 may result in an increase in site options on the body of the user at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

The sensor 15 may be an external sensor that secures to the skin of a user or, in other embodiments, may be an implantable sensor that is located in an implant site within the body of the user. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user and enzymes and/or electronics reactive to a biological condition, such as blood glucose level or the like, of the user. In this manner, the delivery device 12 may be provided with sensor data from the sensor 15 secured to the user at a site remote from the location at which the delivery device 12 is secured to the user.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (un-used) disposable housing 20 for further delivery operation with a user.

Figure 3:
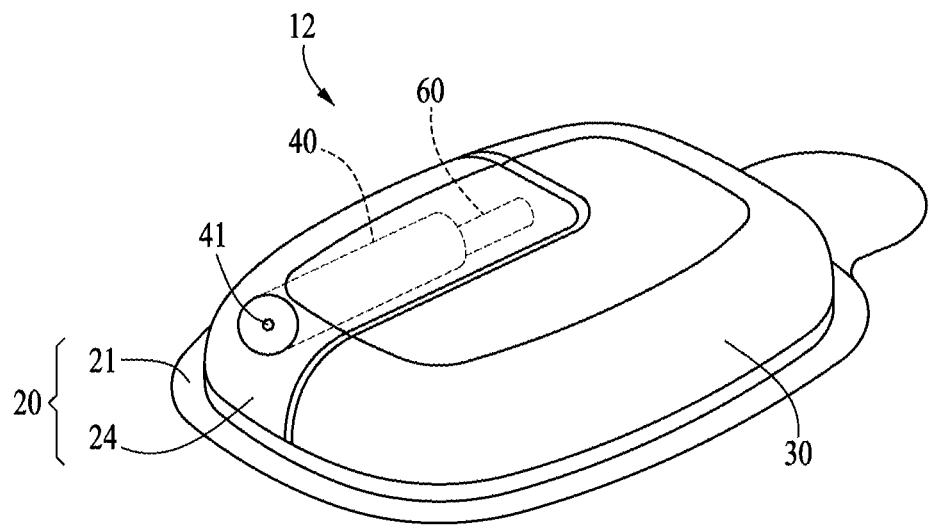
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir 40, the delivery device 12 in the embodiment of FIG. 3 provides for the durable housing 30 to secure to the disposable housing 20 without covering the reservoir 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user. The reservoir retaining portion 24 of the disposable housing 20 is configured to house the reservoir 40. The reservoir retaining portion 24 of the disposable housing 20 may be configured to have an opening to allow for the port 41 of the reservoir 40 to be accessed from outside of the reservoir retaining portion 24 while the reservoir 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir 40.

Figure 4:
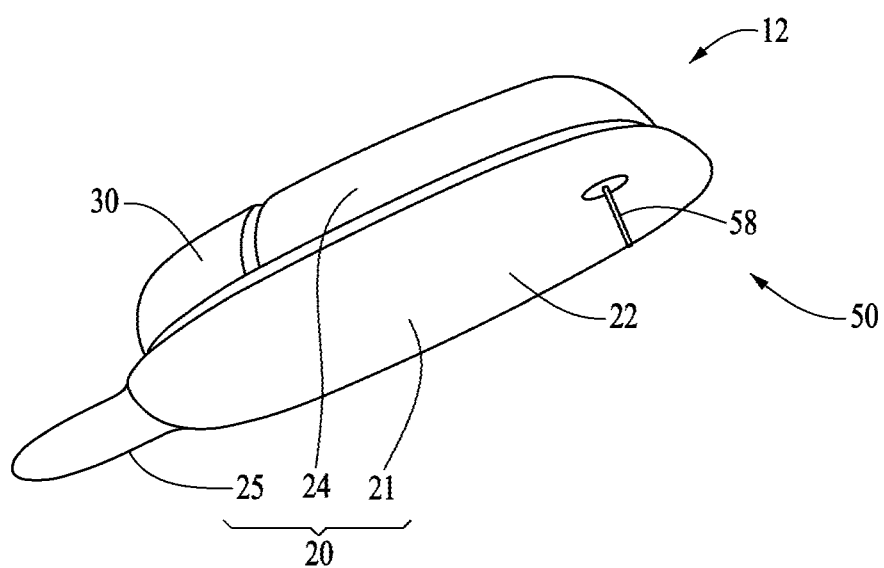
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user under the base 21, when extended. In this manner, the needle 58 may be used to pierce the skin of the user and deliver fluidic media to the user.

Alternatively, the needle 58 may be extended through a hollow cannula (not shown in FIG. 4), such that upon piercing the skin of the user with the needle 58, an end of the hollow cannula is guided through the skin of the user by the needle 58. Thereafter, the needle 58 may be removed, leaving the hollow cannula in place, with one end of the cannula located within the body of the user and the other end of the cannula in fluid flow connection with fluidic media within the reservoir 40, to convey pumped infusion media from the reservoir 40 to the body of the user.

Figure 5A:
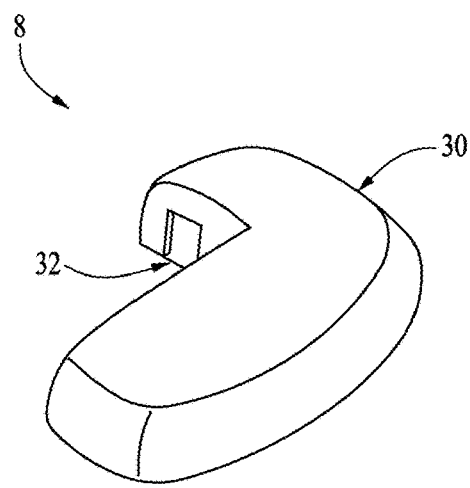
FIG. 5A illustrates a durable portion of a delivery device in accordance with an embodiment of the present invention.
Figure 5B:
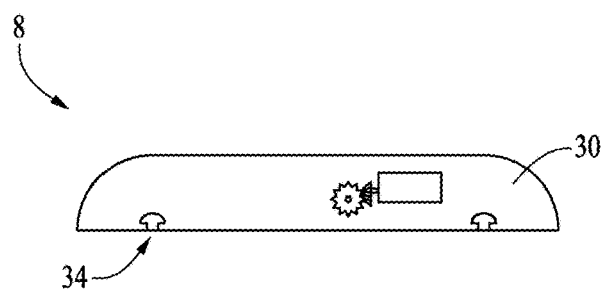
FIG. 5B illustrates a section view of a durable portion of a delivery device in accordance with an embodiment of the present invention.
Figure 5C:
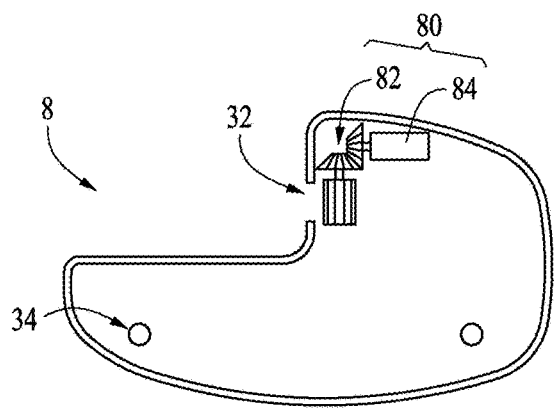
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82. In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
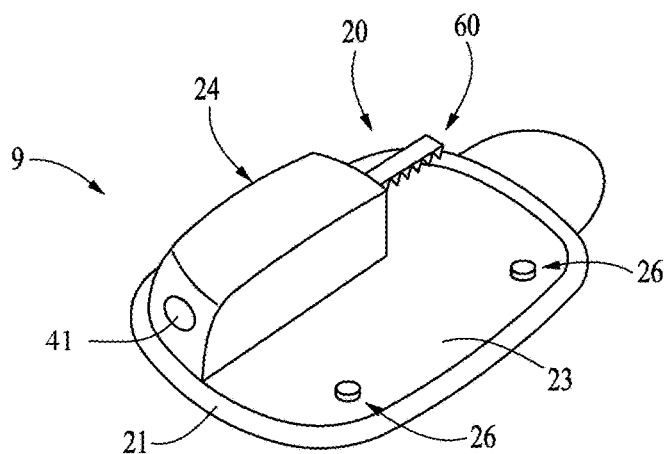
FIG. 6A illustrates a disposable portion of a delivery device in accordance with an embodiment of the present invention.
Figure 6B:
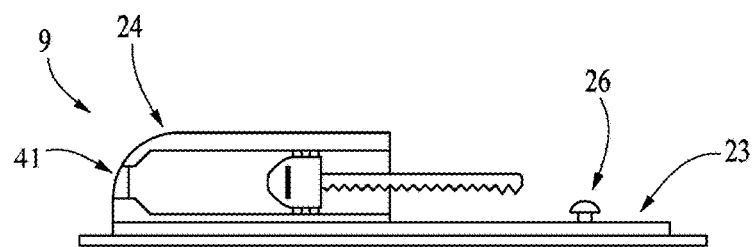
FIG. 6B illustrates a section view of a disposable portion of a delivery device in accordance with an embodiment of the present invention.
Figure 6C:
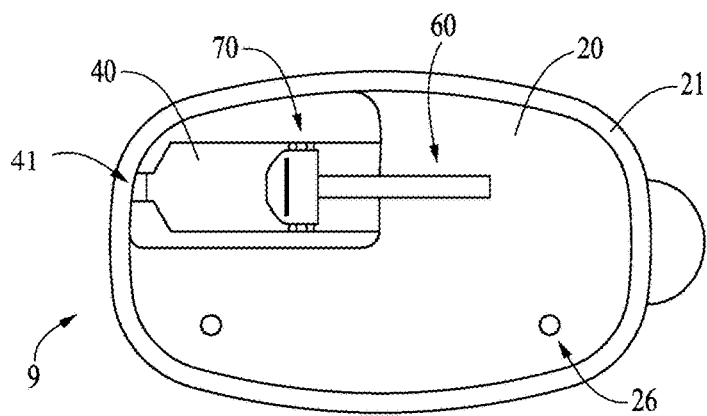
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir 40 is housed within the reservoir retaining portion 24 of the disposable housing 20, and the reservoir 40 is configured to hold fluidic media. Also, in various embodiments, the plunger head 70 is disposed at least partially within the reservoir 40 and is moveable within the reservoir 40 to allow fluidic media to fill into the reservoir 40 and to force fluidic media out of the reservoir 40. In some embodiments, the plunger arm 60 is connected to or is connectable to the plunger head 70. Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir 40. When the interior volume of the reservoir 40 is filled with fluidic media and an infusion path is provided from the reservoir 40 to the body of a user, the plunger head 70 may be moved within the reservoir 40 to force fluidic media from the reservoir 40 and into the infusion path, so as to deliver fluidic media to the body of the user.

In various embodiments, once the reservoir 40 has been sufficiently emptied or otherwise requires replacement, a user may simply remove the durable housing 30 from the disposable housing 20, and replace the disposable portion 9, including the reservoir 40, with a new disposable portion having a new reservoir. The durable housing 30 may be connected to the new disposable housing of the new disposable portion, and the delivery device including the new disposable portion may be secured to the skin of a user. In various other embodiments, rather than replacing the entire disposable portion 9 every time the reservoir 40 is emptied, the reservoir 40 may be refilled with fluidic media. In some embodiments, the reservoir 40 may be refilled while remaining within the reservoir retaining portion 24 (refer to FIG. 6B) of the disposable housing 20. Also, in various embodiments, the reservoir 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir 40 includes reservoir circuitry (not shown). In various embodiments, the reservoir circuitry stores information such as, but not limited to, at least one of (i) an identification string identifying the reservoir 40; (ii) a manufacturer of the reservoir 40; (iii) contents of the reservoir 40; and (iv) an amount of contents in the reservoir 40. In some embodiments, the delivery device 12 includes the reservoir status circuitry (not shown), and the reservoir status circuitry is configured to read data from the reservoir circuitry when the reservoir 40 is inserted into the disposable portion 9.

In various embodiments, the reservoir status circuitry is further configured to store data to the reservoir circuitry after at least some of the contents of the reservoir 40 have been transferred out of the reservoir 40, so as to update information in the reservoir circuitry related to an amount of contents still remaining in the reservoir 40. In some embodiments, the reservoir status circuitry is configured to store data to the reservoir circuitry, so as to update information in the reservoir circuitry related to an amount of contents still remaining in the reservoir 40, when the reservoir 40 is inserted into the disposable portion 9. In some embodiments, the delivery device 12 includes the reservoir status circuitry (not shown) and the reservoir 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7A:
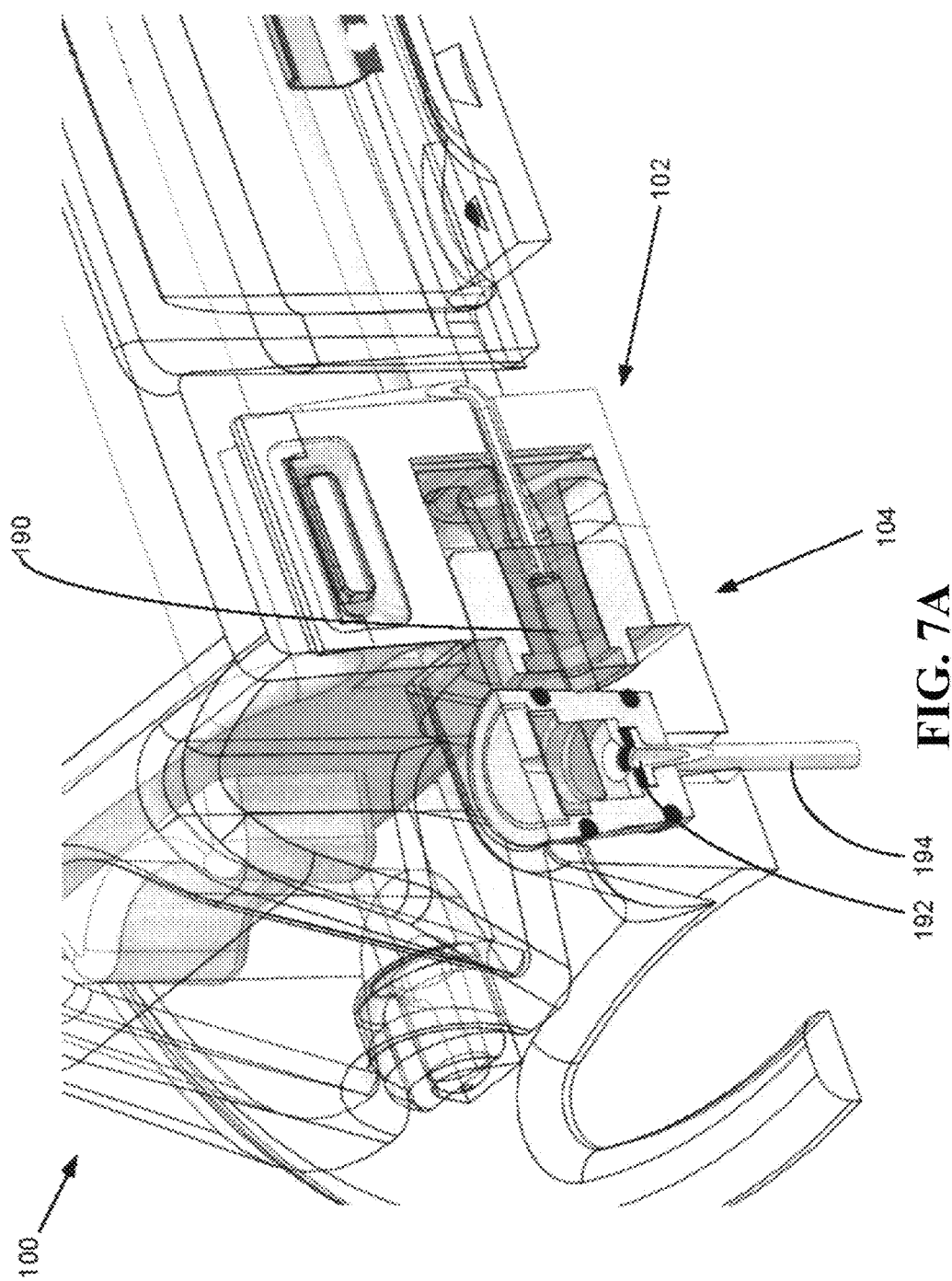
FIG. 7A illustrates a cross-sectional view of a delivery device in accordance with an embodiment of the present invention.

FIG. 7A illustrates a cross-sectional view of a delivery device 100 in accordance with an embodiment of the present invention. The delivery device 100 may include, but not limited to, a reservoir assembly 102 and a base assembly 104. The reservoir assembly 102 and the base assembly 104 may be configured to be connected to and disconnected from one another by the user. The base assembly 104, which may be adapted to be carried by the user, may include a fluid path 190 for receiving fluidic media from the reservoir assembly 102. The base assembly 104 may also include a subcutaneous cannula 194 or catheter having a needle path 192 to allow an injection needle (not shown) to pierce the skin of the user and allow fluidic media to flow into the body of a patient.

Figure 7B:
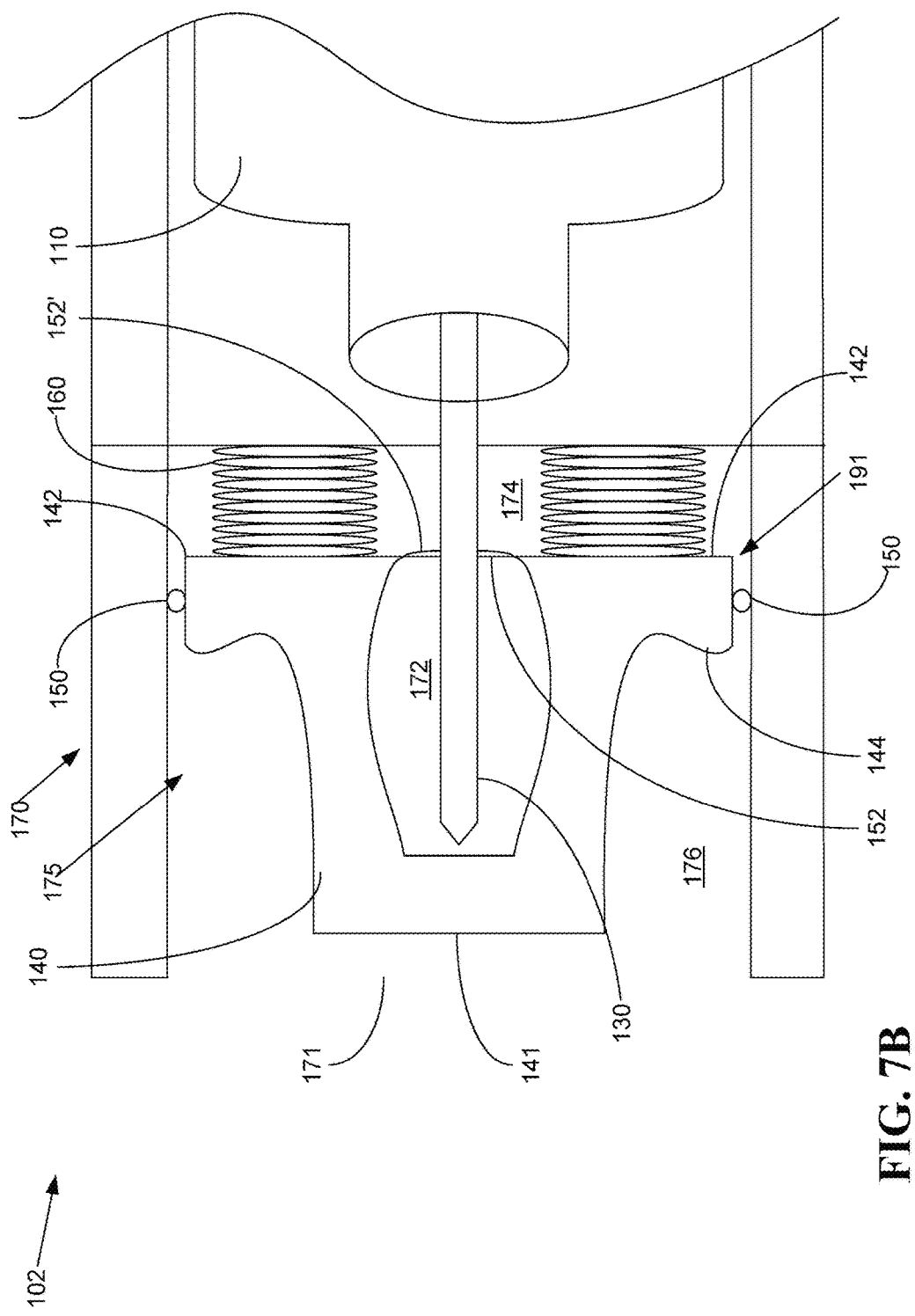
FIG. 7B illustrates a cross-sectional view of a reservoir assembly in accordance with an embodiment of the present invention.

FIG. 7B illustrates a cross-sectional view of the reservoir assembly 102 in accordance with an embodiment of the present invention. With reference to FIGS. 7A and 7B, the reservoir assembly 102 may include a reservoir 110 and a first structure 170 having a chamber 175. The reservoir 110 may contain fluidic media, such as, but not limited to, insulin or the like. The first structure 170 may include a needle 130 and a pierceable member 140. The needle 130 may be connected to the reservoir 110 for allowing fluidic media contained in the reservoir 110 to flow through the needle 130 when the needle 130 is connected to the reservoir 110. The needle 130 may have a longitudinal dimension and a central axis along the longitudinal dimension of the needle 130.

The pierceable member 140 may be located within the chamber 175. The pierceable member 140 may be moveable within the chamber 175 along the longitudinal dimension of the needle 130. The pierceable member 140 may have an interior volume 172 for containing fluidic media expelled from the reservoir 110 before the pierceable member 140 is pierced by the needle 130. In some embodiments of the present invention, the interior volume 172 of the pierceable member 140 may be for containing fluidic media that flows through the needle 130 from the reservoir 110 before the pierceable member 140 is pierced by the needle 130.

In some embodiments of the present invention, the pierceable member 140 may have a cross-section that is U-shaped. In some embodiments of the present invention, the pierceable member 140 may be made of a resealable material. Thus when the user disconnects the reservoir assembly 102 from the base assembly 104, for example to replace an empty reservoir with a new reservoir, the needle 130 is retracted or otherwise removed from the pierceable member 140 and the pierceable member 140 is resealed. As a result, fluidic media contained in the interior volume 172 of the pierceable member 140 may continue to be contained within the interior volume 172 of the pierceable member 140. Once the new reservoir is installed, the interior volume 172 of the pierceable member 140 may be used to contain fluidic media expelled from the new reservoir before the needle 130 again pierces the pierceable member 140.

Figure 13:
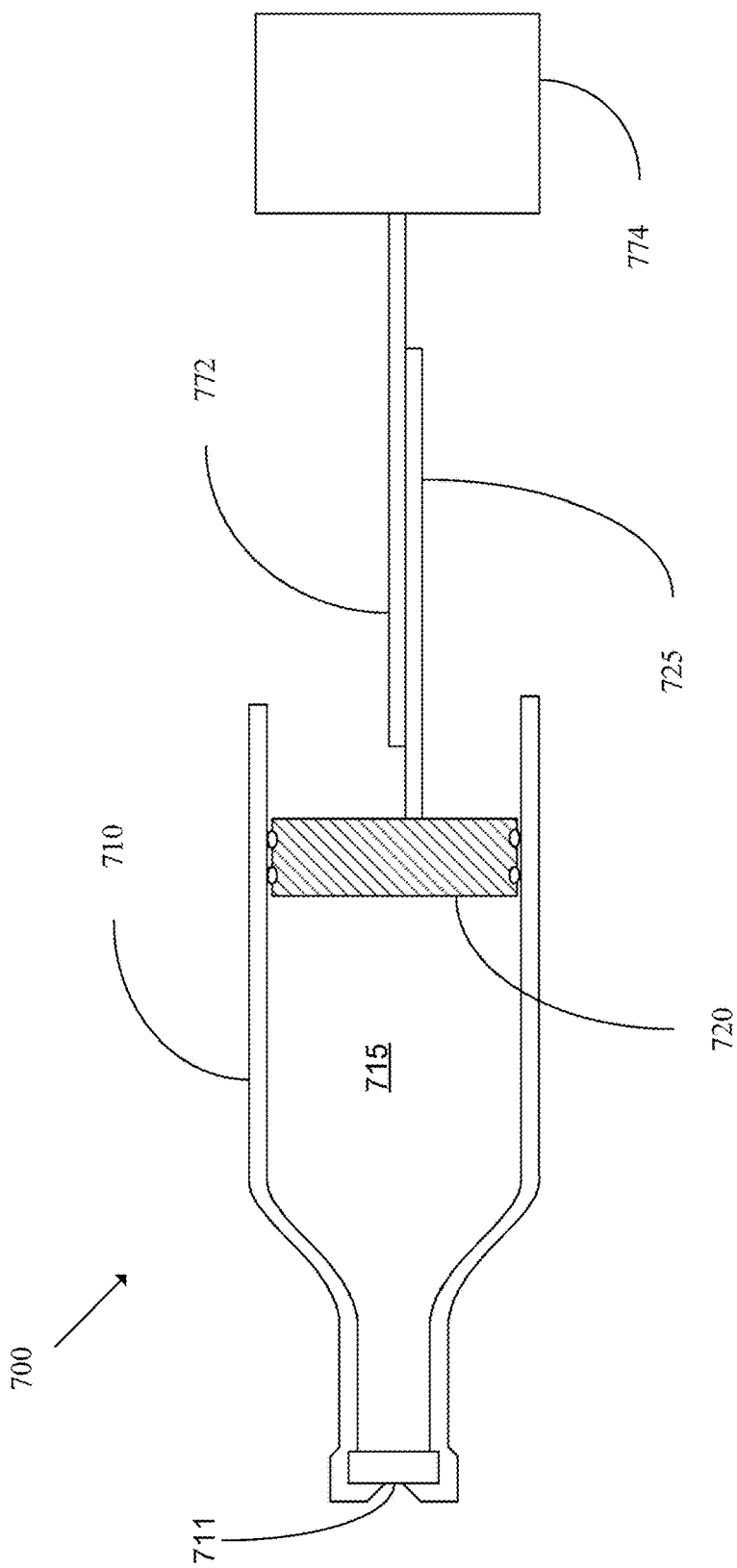
FIG. 13 illustrates a cross-sectional view of a conventional pump delivery device.

Fluidic media may be expelled from the reservoir 110 before the pierceable member 140 is pierced by the needle 130 when a pressure difference exists between the reservoir 110 and the chamber 175. This may be due to an external influence such as an altitude or a temperature change or imperfect alignment of a plunger shaft 725 (refer to FIG. 13) and a driveshaft 772 (refer to FIG. 13). In such a case, fluidic media may flow or bolus from the reservoir 110 into the interior volume 172 of the pierceable member 140 until pressure in the reservoir 110 has been sufficiently equalized relative to pressure in the chamber 175. Thus, preventing the user from inadvertently being administered fluidic media, which could harm the user. Once pressure has been sufficiently equalized, fluidic media may be inhibited from flowing through the needle 130 until directed by the delivery device, for example, to satisfy the need of the user. In some embodiments, fluidic media may be expelled from the reservoir 110 before the pierceable member 140 is pierced by the needle 130 in a case where a pressure difference exists between the reservoir 110 and the interior volume 172 of the pierceable member 140.

The pierceable member 140 may have a first end 141 and a second end 142 on an opposite side of the pierceable member 140 from the first end 141. The pierceable member 140 may be positioned in the chamber 175 relative to the needle 130 so that the needle 130 can pierce the pierceable member 140 when the user connects the reservoir assembly 102 with the base assembly 104. Connecting the reservoir assembly 102 with the base assembly 104 may cause the base assembly 104 to push against the first end 141 of the pierceable member 140. As a result, the pierceable member 140 is pushed against the needle 130 causing the needle 130 to pierce through the pierceable member 140. The needle 130 may be positioned to pierce through the pierceable member 140 and enter the fluid path 190 of the base assembly 104 when the user connects the reservoir assembly 102 with the base assembly 104. In some embodiments, an end of the needle 130 may be located at least substantially within the interior volume 172 of the pierceable member 140 before the needle 130 pierces the pierceable member 140. This may help ensure that fluidic media that flows through the needle 130 before piercing the pierceable member 140 is collected in the interior volume 172 of the pierceable member 140.

In some embodiments of the present invention, the chamber 175 may include a first chamber 174. The first chamber 174 may be adjacent to the second end 142 of the pierceable member 140. In other embodiments of the present invention, the first chamber 174 may be located between the pierceable member 140 and the reservoir 110. The first chamber 174 may contain fluidic media that flows out, or otherwise escapes, from the interior volume 172 of the pierceable member 140. For example, this could occur in a case where a volume of fluidic media expelled from the reservoir 110 exceeds a capacity of the interior volume 172 of the pierceable member 140. The excess fluidic media could then flow into the first chamber 174 and be contained therein. As a further example, fluidic media could escape from the interior volume 172 of the pierceable member 140 in a case where fluidic media enters the interior volume 172 too quickly causing fluidic media to flow out of the interior volume 172 into the first chamber 174.

In further embodiments of the present invention, the chamber 175 may include a second chamber 176. The second chamber 176 may be located on an opposite side of the pierceable member 140 from the first chamber 174, such as adjacent to the first end 141 of the pierceable member 140. The pierceable member 140 may be located between the first chamber 174 and the second chamber 176. The second chamber 176 may contain fluidic media that flows out, or otherwise escapes, from the first chamber 174. For example, this could occur in a case where the first chamber 174 fills with fluidic media. The excess fluidic media could then flow between the pierceable member 140 and the structure 170 into the second chamber 176. As a further example, fluidic media could escape from the first chamber 174 in a case where fluidic media enters the first chamber 174 too quickly causing fluidic media to flow out of the first chamber 174 into the second chamber 176. In yet further embodiments of the present invention, the pierceable member 140 may include a seal member 144 around the pierceable member 140. The seal member 144, for example, may aid in inhibiting fluidic media in the second chamber 176 from flowing back into the first chamber 174. In some embodiments, the seal member 144 may be an annular ring that encircles the pierceable member 140.

In yet further embodiments of the present invention, the structure 170 may include an opening 171 in flow communication with the chamber 175. The opening 171 may be for purging fluidic media that flows out, or otherwise escapes, from the interior volume 172 of the pierceable member 140. For example, this could occur in a case where a volume of fluidic media expelled from the reservoir 110 exceeds the capacity of the interior volume 172 of the pierceable member 140. The excess fluidic media may then flow into the chamber 175 and flow out the opening 171 of the structure 170.

In some embodiments of the present invention, the pierceable member 160 may include a membrane wall 152, which may comprise an elastomeric material, or the like. The membrane wall 152 may be configured to expand 152' to increase the volume of the interior volume 172 of the pierceable member 140 in a case where the interior volume 172 of the pierceable member 140 sufficiently fills with fluidic media. This may be useful in a case where the interior volume 172 of the pierceable member 140 is not sufficiently large enough to contain fluidic media expelled from the reservoir 110. The membrane wall 152 may be for inhibiting fluidic media contained in the interior volume 172 of the pierceable member 140 from flowing out of or otherwise escaping from the interior volume 172 of the pierceable member 140. The membrane wall 152 may also be configured to allow for pressure equalization across it through the use of a hydrophobic or hydrophilic filter or similar material.

Figure 7C:
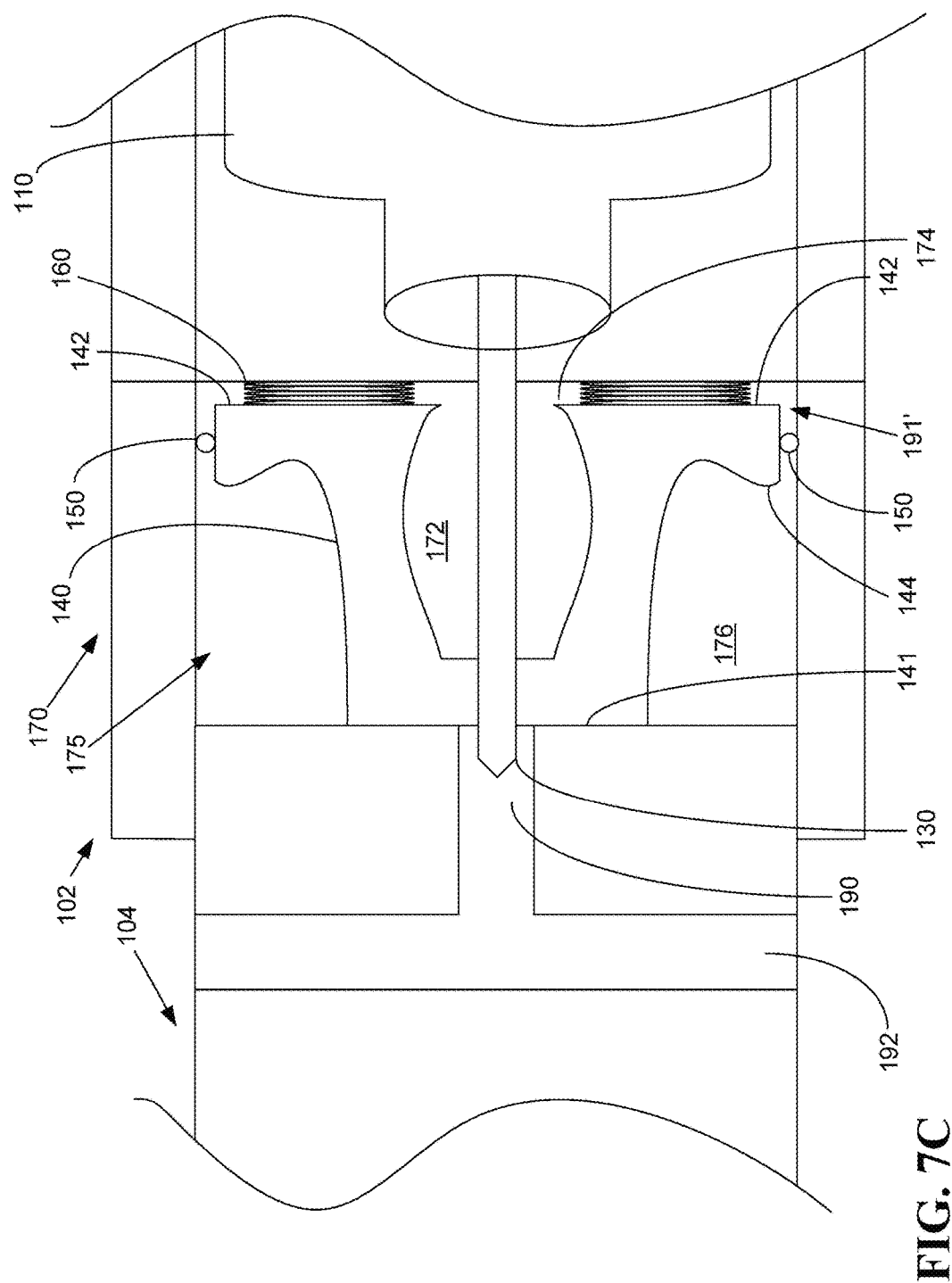
FIG. 7C illustrates a cross-sectional view of a reservoir assembly connected to a base assembly in accordance with an embodiment of the present invention.

With reference to FIGS. 7B and 7C, in some embodiments of the present invention, the reservoir assembly 102 may include a bias member 160. The bias member 160 may be arranged to impart a bias force on the pierceable member 140 as, for instance, the base assembly 104 is pushed against the first end 141 of the pierceable member 140 when the user connects the reservoir assembly 102 with the base assembly 104. As a result, the pierceable member 140 can be moved from a first position 191 to a second position 191'. Additionally, the pierceable member 140 may be moved to various positions between the first position 191 and the second position 191', as well as positions beyond the second position 191'. In some embodiments of the present invention, the bias member 160 may be, but is not limited to, a spring or the like.

In further embodiments of the present invention, the pierceable member 140 may have a resiliently flexible portion (not shown) for providing a bias force on the pierceable member 140. In various embodiments, the bias function may be integral to the pierceable member 140, a function of the resiliently flexible portion (not shown), which may be made of a material such as rubber, or the like. The flexible portion (not shown) may, for example, compress allowing the pierceable member 140 to move within the chamber 175 from the first position 191 to the second position 191' when the user connects the base assembly 104 with the reservoir assembly 102 and uncompress when the user disconnects the base assembly 104 and the reservoir assembly 102 returning the pierceable member 140 to the first position 191.

In alternative embodiments, the needle 130 may be supported by the base assembly 104 and positioned to pierce the pierceable member 140 and enter the reservoir 110. The interior volume 172 of the pierceable member 140 may contain fluidic media expelled from the reservoir 110 before the pierceable member 140 is pierced by the needle 130.

In some embodiments of the present invention, the interior volume 172 of the pierceable member 140 may be curved concavely relative to the central axis of the needle 130. This may increase the capacity of the interior volume 172 of the pierceable member 140 to hold more fluidic media. Furthermore, this may allow more fluidic media to be contained within the interior volume 172 of the pierceable member 140 when the reservoir assembly 102 is orientated on its side, for example, when the central axis of the needle 130 is parallel to an infusion site (not shown) as may be a case in FIGS. 7A-7C. In further embodiments of the present invention, the system 100 may include a seal member, such as an o-ring 150 or the like located between the structure 170 and the pierceable member 140 to facilitate movement of the pierceable member 140 within the chamber 175. In some embodiments, the o-ring 150 may substantially prevent fluidic media from flowing between the pierceable member 140 and the structure 170.

FIG. 7C illustrates a cross-sectional view of the reservoir assembly 102 connected to the base assembly 104 in accordance with an embodiment of the present invention. Once pressure in the reservoir 110 has been sufficiently equalized, the user may connect the reservoir assembly 102 with the base assembly 104. When the user connects the reservoir assembly 102 and the base assembly 104, the base assembly 104 is pushed against the first end 141 of the pierceable member 140. This forces the pierceable member 140 against the bias member 160 and moves the pierceable member 140 from the first position 191 (refer to FIG. 7B) to the second position 191' causing the needle 130 to pierce through the pierceable member 140 and enter the fluid path 190 of the base assembly 104. As a result, fluidic media can flow from the reservoir 110 through the needle 130 into the fluid path 190 and into the user by way of the needle path 192 and cannula 194 (refer to FIG. 7A) as required by the user.

Fluidic media expelled from the reservoir 110 and collected in the interior volume 172 of the pierceable member 140 before the needle 130 pierces the pierceable member 140 may remain in the interior volume 172 of the pierceable member 140. In other embodiments, fluidic media expelled from the reservoir 110 before the needle 130 pierces the pierceable member 140 may remain in at least one of the interior volume 172 of the pierceable member 140, the first chamber 174, or the second chamber 176.

FIG. 8A illustrates a cross-sectional view of a system 200 for equalizing pressure in a first position in accordance with an embodiment of the present invention. The system 200 may include, but is not limited to, a reservoir assembly 202 and a base assembly 204. The reservoir assembly 202 may include a reservoir 210 having a port 212 and a septum 214, a plug 240, and a structure 255 having a chamber 250. The base assembly 204, which may be adapted to be carried by the user, may include a needle 230. The needle 230 may be for piercing the septum 214 of the reservoir 210 when the user connects the base assembly 204 with the reservoir assembly 202. The needle 230 may be for allowing fluidic media contained in the reservoir 210 to flow through the needle 230 into the base assembly 204 when the needle 230 is connected to the reservoir 210 when, for example, the needle 230 pierces the septum 214 and enters the reservoir 210.

The reservoir 210 may have an interior volume 215 for containing fluidic media, such as, but not limited to, insulin. The port 212 of the reservoir 210 may be for allowing fluidic media to be expelled from the reservoir 210 in a case where a pressure difference exists between the interior volume 215 of the reservoir 210 and the chamber 250. As discussed, this could be due, but is not limited to, an external influence such as an altitude or a temperature change or imperfect alignment of a plunger shaft 225 and a driveshaft 272 when the reservoir 210 is installed into the delivery device.

The plug 240 may be positioned relatively offset to the port 212 of the reservoir 210. The plug 240 may be for closing the port 212 of the reservoir 210 when the plug 240 is in a closed position. For example, when the user connects the reservoir assembly 202 and the base assembly together 204, the base assembly 204 forces the plug 240 into or over the port 212 of the reservoir 210 to close the port 212, thus preventing fluidic media in the interior volume 215 of the reservoir 210 from flowing out the port 212 of the reservoir 210. The plug 240 may be, but is not limited to, a flapper valve, a disc valve, or the like.

The chamber 250 of the structure 255 may be connected to the reservoir 210. The chamber 250 may be for collecting fluidic media expelled from the interior volume 215 of the reservoir 210 in a case where a pressure difference exists between the interior volume 215 of the reservoir 210 and the chamber 250. As shown in FIG. 8A, the plug 240 initially may be in an open position so that the port 212 is at least partially unobstructed so that fluidic media can flow freely or bolus through the port 212 into the chamber 250 in a case where a pressure difference exists between the interior volume 215 of the reservoir 210 and the chamber 250. Fluidic media may flow through the port 212 until pressure within the interior volume 215 of the reservoir 210 has been sufficiently equalized relative to pressure in the chamber 250. In other embodiments, the plug 240 may be located at least partially in or over the port 212 and may be positioned to be forced away from the port 212 by the expelled fluidic media. Once pressure in the interior volume 215 of the reservoir 210 has been sufficiently equalized, the reservoir assembly 202 may be connected with the base assembly 204.

Figure 8C:
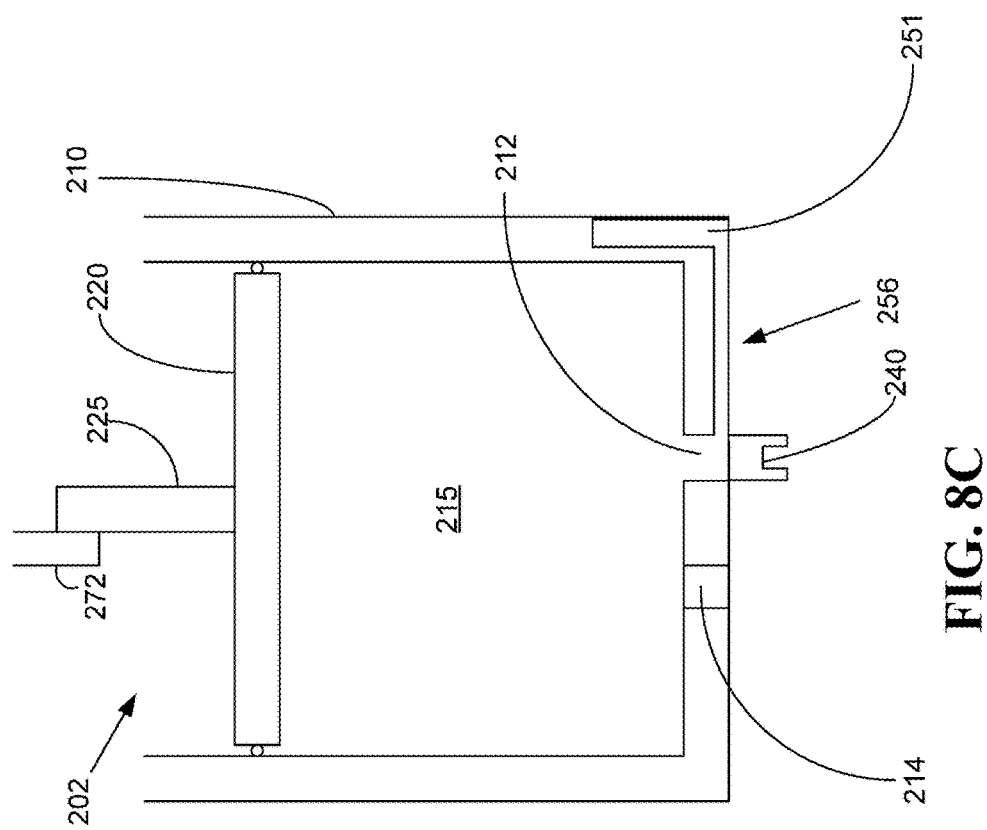
FIG. 8C illustrates a cross-sectional view of a reservoir in accordance with an embodiment of the present invention.

The structure 255 having the chamber 250 may be located outside of the reservoir 210. For example, the chamber 250 may be adjacent to the reservoir 210. In other embodiments, such as the embodiment illustrated in FIG. 8C, a structure 256 having a chamber 251 may be located within the reservoir 210. With reference to FIG. 8A, in further embodiments of the present invention, the structure 255 may include a membrane wall 252, which may comprise an elastomeric material, or the like. The membrane wall 252 may also be configured to allow for pressure equalization across it through the use of a hydrophobic or hydrophilic filter or similar material. The membrane wall 252 may be configured to expand (252' in FIG. 8B) to increase the volume of the chamber 250 in a case where the chamber 250 sufficiently fills with fluidic media. In yet further embodiments of the present invention, the structure 255 may have an opening (not shown) in communication with the chamber 250 for purging fluidic media collected in the interior volume of the chamber 250. This may be useful in a case where the interior volume of the chamber 250 is not sufficiently large enough to contain fluidic media expelled from the interior volume 215 of the reservoir 210.

FIG. 8B illustrates a cross-sectional view of the system 200 for relieving pressure in a second position in accordance with an embodiment of the present invention. Once pressure in the interior volume 215 of the reservoir 210 has been sufficiently equalized, the user may place the system 200 in the second position by connecting the reservoir assembly 202 with the base assembly 204. In the second position of the system 200, the plug 240 may be in a closed position so that the port 212 of the reservoir 210 is substantially closed, such that fluidic media in the interior volume 215 of the reservoir 210 can no longer flow into the chamber 250. The port 212 may be closed by the plug 240 when the user connects the reservoir assembly 202 with the base assembly 204. In such a case, the base assembly 204 pushes against the plug 240 of the reservoir assembly 202 and forces the plug 240 to enter, or otherwise cover, the port 212 of the reservoir 210 of the reservoir assembly 202. The plug 240 may be held in or against the port 212 by the base assembly 204. The plug 240 may cover the port 212 of the reservoir 210, and fluidic media contained in the chamber 250 may remain isolated from fluidic media contained in the interior volume 215 of the reservoir 210. In some embodiments of the present invention, the base assembly 204 and the reservoir assembly 202 are not connected until pressure in the interior volume 215 of the reservoir 210 has been equalized with respect to pressure in the chamber 250.

According to the embodiment illustrated in FIG. 8B, when the user connects the reservoir assembly 202 and the base assembly 204 together, the needle 230, which may be supported by the base assembly 204, pierces the septum 214 of the reservoir 210 and enters the reservoir 210. As a result, fluidic media contained in the interior volume 215 of the reservoir 210 can flow through the needle 230 into the base assembly 204 and ultimately to the user. For example with reference to FIGS. 7A and 8B, fluidic media in the interior volume 215 of the reservoir 210 may flow through the needle 230 into a fluid path 190 into the needle passage 192 and then the cannula 194 and into the user. In other embodiments of the present invention, the needle 230 may be positioned to pierce the plug 240 and enter the reservoir 210. Thus establishing a path for fluidic media in the interior volume 215 of the reservoir 210 to flow through the needle 230 into the base assembly 204 and then to the user. In further embodiments, the reservoir 210 may have a second port (not shown) for delivering fluidic media contained in the interior volume 215 of the reservoir 210 to the base assembly 204 while the reservoir assembly 202 and the base assembly 204 are connected.

Figure 9C:
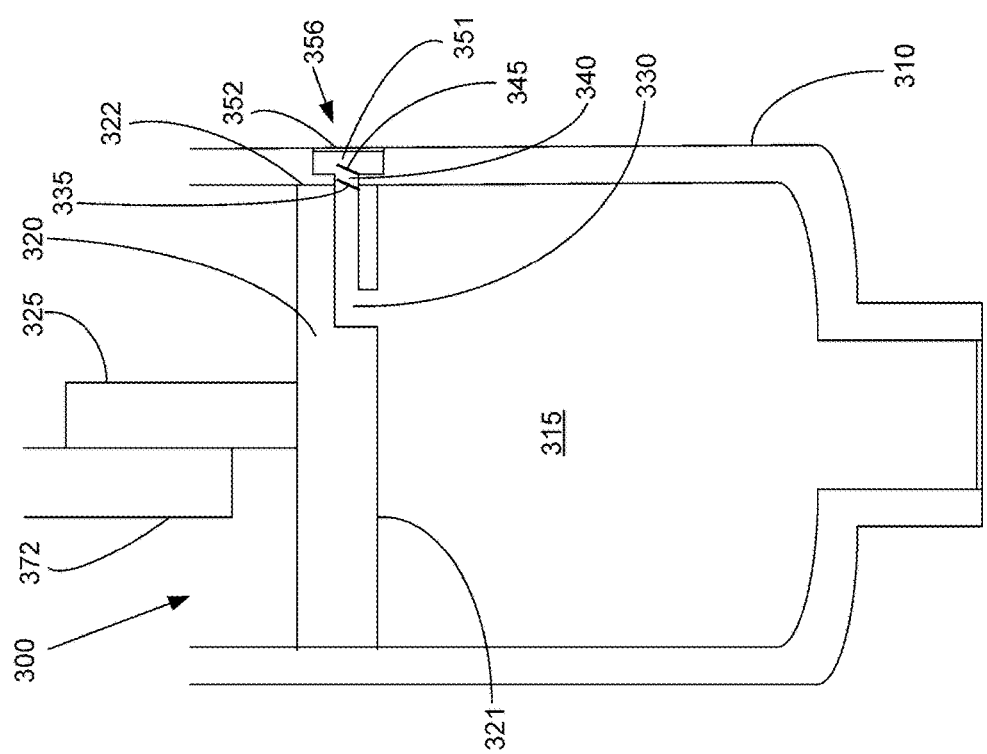
FIG. 9C illustrates a cross-sectional view of a reservoir in accordance with an embodiment of the present invention.

FIG. 9A illustrates a cross-sectional view of a system 300 for equalizing pressure in accordance with an embodiment of the present invention. The system 300 may include, but is not limited to, a reservoir 310 and a plunger head 320. The reservoir 310 may have an interior volume 315 for containing fluidic media, such as, but not limited to, insulin. The reservoir 310 may have a passage 340 for allowing fluidic media to be expelled from the interior volume 315 of the reservoir 310 in a case where a pressure difference exists between the interior volume 315 of the reservoir 310 and the passage 340.

The plunger head 320 may be located within the reservoir 310 and may be moveable within the reservoir 310 to expand or contract the interior volume 315 of the reservoir 310. The plunger head 320 may be connected to a plunger shaft 325. The plunger shaft 325 may comprise, for example, a half-nut, a quarter-nut, a U-shaped nut, or the like, that is able to engage a driveshaft 372 mechanically coupled to a motor (not shown). The driveshaft 372 may be, for example, a partial screw or the like. The plunger head 320 may have a first surface 321 and a second surface 322 connected by a channel 330. The plunger head 320 may be moveable within the reservoir 310 to align the channel 330 with the passage 340. When the channel 330 and the passage 340 are aligned and a pressure difference exists between the interior volume 315 of the reservoir 310 and the passage 340, fluidic media may be expelled from the interior volume 315 of the reservoir 310 through the passage 340.

In some embodiments of the present invention, the reservoir 310 may have a second interior volume 317. The interior volume 315 of the reservoir 310 may allow for containing fluidic media. The plunger head 320 may be located between the interior volume 315 of the reservoir 310 and the second interior volume 317 of the reservoir 310. As the plunger head 320 is advanced within the reservoir 310, the interior volume 315 may be decreased, while the second interior volume 317 may be increased. The first surface 321 of the plunger head 320 may be in contact with fluidic media when fluidic media is in the interior volume 315 of the reservoir 310.

In some embodiments of the present invention, the first surface 321 of the plunger head 320 may be perpendicular to the second surface 322 of the plunger head 320. For example, in the embodiment illustrated in FIG. 9A, when the channel 330 and the passage 340 are aligned and a pressure difference exists between the interior volume 315 of the reservoir 310 and the passage 340, fluidic media expelled from the interior volume 315 of the reservoir 310 may flow into the channel 330 and flow out the passage 340 located on a side of the reservoir 310. In further embodiments of the present invention, the system 300 may include a seal member (not shown), such as an o-ring or the like, located between the plunger head 320 and the reservoir 310 to facilitate movement of the plunger head 320 within the reservoir 310 and to prevent from fluidic media from flowing between the plunger head 320 and the reservoir 310.

The plunger head 320 may be moveable within the reservoir 310 from a first position 390 to a second position 390' (refer to FIG. 9B). In some embodiments, when the plunger head 320 is in the first position 390, the channel 330 and the passage 340 are aligned to establish a flow path from the interior volume 315 of the reservoir 310 through the channel 330 of the plunger head 320 to the passage 340 of the reservoir 310. In a case where the channel 330 and the passage 340 are aligned and a pressure difference exists between the interior volume 315 of the reservoir 310 and the passage 340, fluidic media in the interior volume 315 of the reservoir 310 can flow freely or bolus through the channel 330 into the passage 340 until pressure in the interior volume 315 of the reservoir 310 is sufficiently equalized with respect to pressure in the passage 340. In the second position 390' (refer to FIG. 7B), the passage 340 and the chamber 330 are disaligned (i.e., no longer aligned) so that fluidic media can no longer flow from the interior volume 315 of the reservoir 310 through the passage 340.

In some embodiments of the present invention, such as the embodiment shown in FIG. 9D, the system 300 may include a reservoir assembly 302 and a base assembly 304. The reservoir assembly 302 may support the reservoir 310. The reservoir assembly 302 can be removably attachable to the base assembly 304. With reference to FIGS. 9A and 9B, the plunger head 320 may be advanceable within the reservoir 310 from the first position 390, where the passage 340 and the channel 330 are aligned, to the second position 390', where the passage 340 and the channel 330 are disaligned, before the user connects the base assembly 304 to the reservoir assembly 302. The plunger head 320 may be advanced, for example, manually by the user, or by a motor (not shown) attached to the driveshaft 372. In such an embodiment, the reservoir 310, having the plunger head 320 in the second position 390', would be ready to administer fluidic media safely to the user as needed. Moreover, because fluidic media can no longer flow into the passage 340, fluidic media may not be wasted when the plunger head 320 is advanced from the second position 390' to another position.

In some embodiments of the present invention, the reservoir 310 may further include a structure 355 having a chamber 350. The chamber 350 of the structure 355 may be connected to the passage 340. The chamber 350 may be for collecting fluidic media that flows through the passage 340. Fluidic media may flow through the passage 340 when the channel 330 and the passage 340 are aligned and a pressure difference exists between the interior volume 315 of the reservoir 310 and the passage 340. The structure 355 having the chamber 350 may be located outside of the reservoir 310, for example, the chamber 350 may be adjacent to the reservoir 310. In other embodiments of the present invention, such as the embodiment illustrated in FIG. 9C, a structure 356 having a chamber 351 may be located within the reservoir 310.

In further embodiments of the present invention, such as the embodiments illustrated in FIGS. 9A and 9B, the structure 355 may include a membrane wall 352, which may comprise an elastomeric material, or the like. The membrane wall 352 may be configured to expand 352' to increase the volume of the chamber 350 in a case where the chamber 350 sufficiently fills with fluidic media. This may be useful in a case where the chamber 350 is not sufficiently large enough to contain fluidic media expelled from the reservoir 310. The membrane wall 352 may also be configured to allow for pressure equalization across it through the use of a hydrophobic or hydrophilic filter or similar material.

In some embodiments of the present invention, a valve 335 may be positioned at an end of the channel 330. The valve 335 may be, but is not limited to, a flapper valve or the like. The valve 335 may be moveable between an open position and a closed position. The valve 335 may be for closing the channel 330 when the valve 335 is in the closed position. The valve 335 may be in the closed position after the plunger head 320 is advanced from the first position 390 to the second position 390' due to an abutting side 311 of the reservoir 310 that may prevent the valve 335 from opening. As a result, fluidic media in the interior volume 315 of the reservoir 310 may be prevented from flowing out the channel 330. In some embodiments, the valve 335 may be in the closed position while the plunger head 320 is in the first position 390 in a case where pressure in the interior volume 315 of the reservoir 310 is relatively equal to pressure in the passage 340, such as after pressure has been equalized or if pressure did not have to be equalized.

In some embodiments of the present invention, a valve 345 may be positioned at an end of the passage 340. The valve 345 may be, but is not limited to, a flapper valve or the like. The valve 345 may be moveable between an open position and a closed position. The valve 345 may be for closing the passage 340 when the valve 345 is in the closed position. The valve 345 may be in the closed position after the plunger head 320 is advanced from the first position 390 to the second position 390'. As a result, fluidic media expelled through the passage 340, while the plunger head 320 was in the first position 390, may be prevented from flowing back into the second interior volume 317 of the reservoir 310. This may be desirable because it may keep the reservoir 310 and the delivery device relatively clean and sanitary. In some embodiments, the valve 345 may be in the closed position while the plunger head 320 is in the first position 390 in a case where pressure in the interior volume 315 of the reservoir 310 is relatively equal to pressure in the passage 340, such as after pressure has been equalized or if pressure did not have to be equalized.

FIG. 9B illustrates a cross-sectional view of the system 300 in accordance with an embodiment of the present invention. Once pressure in the interior volume 315 of the reservoir 310 has been sufficiently equalized with respect to pressure in the passage 340, the plunger head 320 may be sufficiently advanced within the reservoir 310 from the first position 390 (refer to FIG. 9A) to the second position 390'. As a result, the passage 340 and the channel 330 of the plunger head 320 are disaligned (i.e., no longer aligned) so that fluidic media in the interior volume 315 of the reservoir 310 may no longer flow into the passage 340. Accordingly, fluidic media that flows from the interior volume 315 of the reservoir 310 into the channel 330 may be prevented from flowing into the passage 340 or otherwise out of the reservoir 310 by the abutting side 311 of the reservoir 310. In addition, fluidic media expelled through the passage 340 may be isolated from fluidic media contained in the interior volume 315 of the reservoir 310. The reservoir 310 may now be ready to provide fluidic media to the user.

In yet further embodiments, the plunger head 320 need not be advanced from the first position 390 (refer to FIG. 9A) to the second position 390' after pressure in the interior volume 315 of the reservoir 310 has been equalized with respect to pressure in the passage 340. In such an embodiment, the reservoir 310 may be ready to provide fluidic media to the user. For example, when the plunger head 320 is advanced from the first position 390 (refer to FIG. 9A) to satisfy a need of the user, the advancement of the plunger head 320 may be sufficient to disalign the channel 330 and the passage 340 so that the interior volume 315 of the reservoir 310 is no longer in flow communication with the passage 340.

In some embodiments, such as the embodiment illustrated in FIG. 9D, the base assembly 304 may include a needle 380 and a mating piece 370. The needle 380 may be for piercing a septum 314 of the reservoir 310 when the user connects the base assembly 304 with the reservoir assembly 302. The needle 380 may be for allowing fluidic media contained in the interior volume 315 of the reservoir 310 to flow through the needle 380 into the base assembly 304 when the needle 380 is connected to the reservoir 310 when, for example, the needle 380 pierces the septum 314 and enters the interior volume 315 of the reservoir 310. The mating piece 370 may be for covering or blocking the passage 340 when the base assembly 302 and the reservoir assembly 304 are connected so that fluidic media in the interior volume 315 of the reservoir 310 cannot flow out the passage 340 while the reservoir assembly 302 and the base assembly 304 are connected.

Figure 10C:
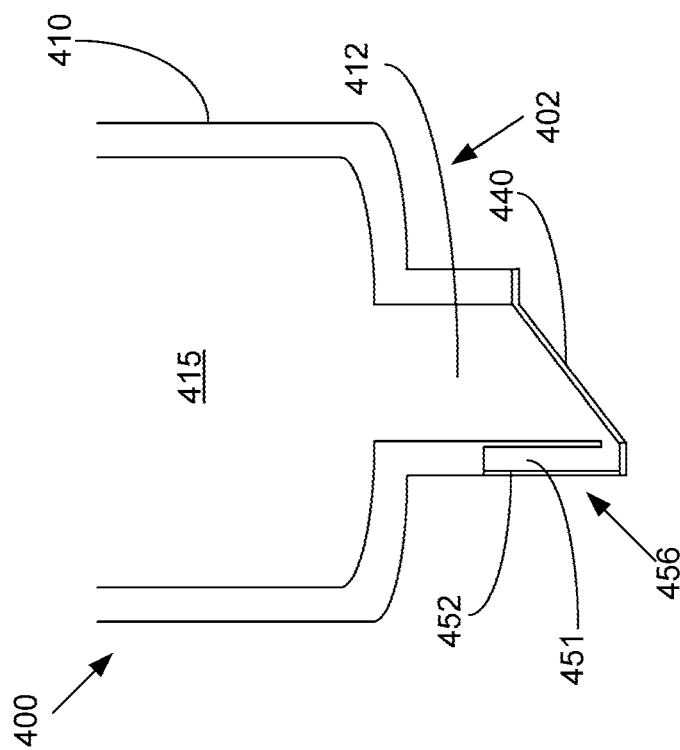
FIG. 10C illustrates a cross-sectional view of a reservoir in accordance with an embodiment of the present invention.

FIG. 10A illustrates a cross-sectional view of a system 400 for equalizing pressure in a first position in accordance with an embodiment of the present invention. The system 400 may include, but is not limited to, a reservoir assembly 402 and a base assembly 404. The reservoir assembly 402 may include a reservoir 410 having a port 412 and a flapper valve 440. The base assembly 404 may include a needle 430 and a mating piece 435. The reservoir 410 may have an interior volume 415 for containing fluidic media, such as, but not limited to, insulin. The port 412 may be an outlet for expelling fluidic media from the interior volume 415 of the reservoir 410 before the mating piece 435 and the reservoir 410 are operatively engaged. The mating piece 435 and the reservoir 410 may be operatively engaged when the user connects the reservoir assembly 402 with the base assembly 404.

The flapper valve 440 may be located on the port 412 of the reservoir 410. The flapper valve 440 may be pierceable by the needle 430. The needle 430 may be supported by the mating piece 435 and positioned to pierce the flapper valve 440 when the user connects the reservoir assembly 402 with the base assembly 404 allowing the needle 430 to enter the interior volume 415 of the reservoir 410 to establish a fluid path between the reservoir assembly 402 and the base assembly 404. The flapper valve 440 may be held against the port 412 by the mating piece 435, thus closing the port 412 when the user connects the reservoir assembly 402 with the base assembly 404.

In some embodiments of the present invention, the system 400 may further include a structure 455 having a chamber 450. The chamber 450 of the structure 455 may be connected to the port 412 of the reservoir 410. In other embodiments, the chamber 450 may be connectable to or otherwise in flow communication with the interior volume 415 of the reservoir 410. For example, when the flapper valve 440 is opened to expel fluidic media, a fluid path may be established between the interior volume 415 of the reservoir 410 and the chamber 450. The chamber 450 may have an interior volume for collecting fluidic media expelled through the port 412 from the interior volume 415 of the reservoir 410 before the mating piece 435 and the reservoir 410 are connected or otherwise operatively engaged. Fluidic media may be expelled from the reservoir 410 before the mating piece 435 and the reservoir 410 are operatively engaged in a case where a pressure difference exists between the interior volume 415 of the reservoir 410 and the chamber 450. The structure 455 having the chamber 450 may be located outside of the reservoir 410. For example, the chamber 450 may be adjacent to the reservoir 410. In some embodiments of the present invention, such as the embodiment illustrated in FIG. 10C, a structure 456 having a chamber 451 may be located within the reservoir 410.

As shown in FIG. 10A, the port 412 of the reservoir 410 may be initially in an open position, such that fluidic media expelled from the reservoir 410 to equalize pressure within the interior volume 415 of the reservoir 410, can flow freely or bolus through the port 412. The expelled fluidic media may force the flapper valve 440 to open and flow out of the interior volume 415 of the reservoir 410 until pressure within the interior volume 415 of the reservoir 410 has been equalized with respect to pressure in the chamber 450.

In some embodiments of the present invention, the structure 455 may include a membrane wall 452, which may comprise an elastomeric material, or the like. The membrane wall 452 may be configured to expand (452' in FIG. 10B) outwardly to increase the interior volume of the chamber 450 in a case where the chamber 450 sufficiently fills with fluidic media. The membrane wall 452 may also be configured to allow for pressure equalization across it through the use of a hydrophobic or hydrophilic filter or similar material. In yet further embodiments of the present invention, the structure 455 may have an opening (not shown) for purging fluidic media collected in the interior volume of the chamber 450. This may be useful in a case where the interior volume of the chamber 450 is not sufficiently large enough to contain all of the fluidic media expelled from the interior volume 415 of the reservoir 410.

FIG. 10B illustrates a cross-sectional view of the system 400 for equalizing pressure in a second position in accordance with an embodiment of the present invention. Once pressure in the interior volume 415 of the reservoir 410 has been sufficiently equalized, the user may connect the reservoir assembly 402 with the base assembly 404. When the user connects the reservoir assembly 402 with the base assembly 404, the mating piece 435 may push the flapper valve 440 against the port 412 to close or block the port 412, such that fluidic media in the interior volume 415 of the reservoir 410 can no longer flow out the port 412 to the chamber 450. The needle 430 pierces the flapper valve 440 to allow fluidic media contained in the interior volume 415 of the reservoir 410 to flow through the needle 430 to the base assembly 404 and then to the user. For example, fluidic media could flow from the interior volume 415 of the reservoir 410 through the needle 430 into a fluid path (such as 190 in FIG. 7A) in the base assembly 404 and to the user by way of a cannula (such as 194 in FIG. 7A).

The mating piece 435 may securely hold the flapper valve 440 against the port 412 to prevent the flapper valve 440 from opening while the reservoir assembly 402 and the base assembly 404 are connected. In some embodiments of the present invention, the mating piece 435 may seal off the chamber 450, thus inhibiting fluidic media contained in the chamber 450 from flowing back into the interior volume 415 of the reservoir 410 or otherwise flowing out of the chamber 450.

FIG. 11A illustrates a cross-sectional view of a system 500 for equalizing pressure in a first position in accordance with an embodiment of the present invention. The system 500 may include, but is not limited to, a reservoir assembly 500 and a base assembly 504. The reservoir assembly 502 may include a reservoir 510 having a port 512 and a cap 540. The base assembly 504 may include a needle 530 and a mating piece 535. The reservoir 510 may have an interior volume 515 for containing fluidic media, such as, but not limited to, insulin. The port 512 may be an outlet for expelling fluidic media from the interior volume 515 of the reservoir 510 before the mating piece 535 and the reservoir 510 are operatively engaged. The mating piece 535 and the reservoir 510 may be operatively engaged when the user connects the reservoir assembly 502 with the base assembly 504.

The cap 540 may be located on the port 512 of the reservoir 510. The cap 540 may be loosely fitted on the port 512 to allow fluidic media in the reservoir 510 to push against the cap 540 and lift the cap 540 from the port 512 and flow out the interior volume 515 of the reservoir 510. In other embodiments, such as the embodiment shown in FIG. 11A, the cap 540 may be positioned relatively offset to the port 512 so that fluidic media may flow freely through the port 512. The cap 540 may be pierceable by the needle 530. The needle 530 may be supported by the mating piece 535 and positioned to pierce the cap 540 when the user connects the reservoir assembly 502 with the base assembly 504 allowing the needle 530 to enter the interior volume 515 of the reservoir 510 to establish a fluid path between the reservoir assembly 502 and the base assembly 504. The cap 540 may be held against the port 512 by the mating piece 535, thus closing the port 512 when the user connects the reservoir assembly 502 with the base assembly 504.

In some embodiments of the present invention, the system 500 may further include a structure 555 having a chamber 550. The chamber 550 of the structure 555 may be connected to the port 512 of the reservoir 510. In other embodiments, the chamber 550 may be connectable or otherwise in flow communication with the interior volume 515 of the reservoir 510. For example, when the cap 540 is lifted from the port 512 to allow fluidic media to be expelled from the interior volume 515 of the reservoir 510, a fluid path may be established from the interior volume 515 of the reservoir 510 to the chamber 550. The chamber 550 may have an interior volume for collecting fluidic media expelled through the port 512 from the interior volume 515 of the reservoir 510 before the mating piece 535 and the reservoir 510 are connected or otherwise operatively engaged. Fluidic media may be expelled from the reservoir 510 before the mating piece 535 and the reservoir 510 are operatively engaged in a case where a pressure difference exists between the interior volume 515 of the reservoir 510 and the chamber 550. The structure 555 having the chamber 550 may be located outside of the reservoir 510, for example, the chamber 550 may be adjacent to the reservoir 510. In other embodiments of the present invention, the structure 555 having the chamber 550 may be located within the reservoir 510.

As shown in FIG. 11A, the port 512 of the reservoir 510 may be initially in an open position, such that fluidic media expelled from the interior volume 515 of the reservoir 510 to equalize pressure within the interior volume 515 of the reservoir 510, can flow freely or bolus through the port 512 into the chamber 550. In some embodiments, the expelled fluidic media may push against the cap 540 to move the cap 540 from the port 512 allowing fluidic media to flow out of the interior volume 515 of the reservoir 510 until pressure in the interior volume 515 of the reservoir 510 has been equalized with respect to pressure in the chamber 550.

In further embodiments of the present invention, the structure 555 may include a membrane wall 552, which may comprise an elastomeric material, or the like. The membrane wall 552 may be configured to expand (552' in FIG. 11B) outwardly to increase the interior volume of the chamber 550 in a case where the chamber 550 sufficiently fills with fluidic media. The membrane wall 552 may also be configured to allow for pressure equalization across it through the use of a hydrophobic or hydrophilic filter or similar material. In yet further embodiments of the present invention, the structure 555 may have an opening (not shown) for purging fluidic media collected in the interior volume of the chamber 550.

FIG. 11B illustrates a cross-sectional view of the system 500 for equalizing pressure in a second position in accordance with an embodiment of the present invention. Once pressure in the interior volume 515 of the reservoir 510 has been sufficiently equalized, the user may connect the reservoir assembly 502 with the base assembly 504. When the user connects the reservoir assembly 502 with the base assembly 504, the mating piece 535 of the base assembly 504 pushes the cap 540 against the port 512 of the reservoir 510 to close or block the port 512. Thus, fluidic media in the interior volume 515 of the reservoir 510 can no longer flow out the port 512 into the chamber 550. The needle 530 pierces the cap 540 to allow fluidic media contained in the interior volume 515 of the reservoir 510 to flow through the needle 530 to the base assembly 504 and then to the user. For example, fluidic media could flow from the interior volume 515 of the reservoir 510 through the needle 530 into a fluid path (such as 190 in FIG. 7A) in the base assembly 504 and to the user by way of a cannula (such as 194 in FIG. 7A).

The mating piece 535 may securely hold the cap 540 against the port 512 to prevent the cap 540 from opening while the reservoir assembly 502 and the base assembly 504 are connected. In some embodiments of the present invention, the mating piece 535 may block or seal off the chamber 550, thus inhibiting fluidic media contained in the chamber 550 from flowing back into the interior volume 515 of the reservoir 510 or otherwise flowing out of the chamber 550.

Figure 12C:
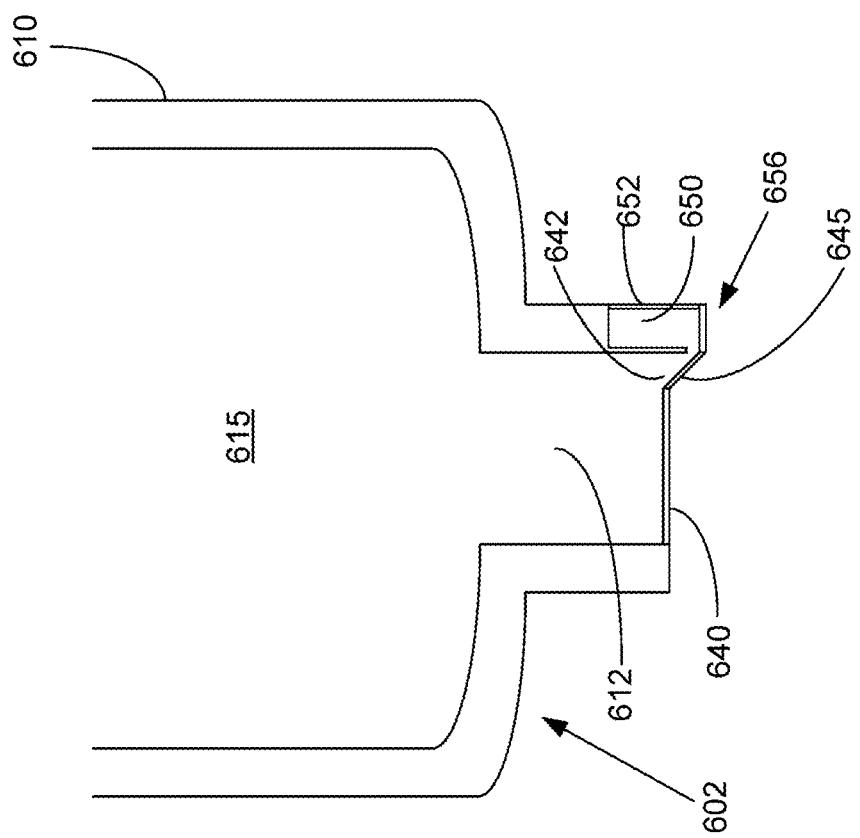
FIG. 12C illustrates a cross-sectional view of a reservoir in accordance with an embodiment of the present invention.

FIG. 12A illustrates a cross-sectional view of a system 600 for equalizing pressure in a first position in accordance with an embodiment of the present invention. The system 600 may include, but is not limited to, a reservoir assembly 602 and a base assembly 604. The reservoir assembly 602 may include a reservoir 610 having a port 612 and a covering 640 having an opening 642. The base assembly 604 may include a needle 630 and a mating piece 635. The reservoir 610 may have an interior volume 615 for containing fluidic media, such as, but not limited to, insulin. The port 612 may be an outlet for expelling fluidic media from the interior volume 615 of the reservoir 610 through the opening 642 in the covering 640 before the mating piece 635 and the reservoir 610 are operatively engaged. Fluidic media may be expelled from the interior volume 615 of the reservoir 610 before the mating piece 635 and the reservoir 610 are operatively engaged, for example, in a case where a pressure difference exists between the interior volume 615 of the reservoir 610 and a chamber 650 attached to the port 612. The mating piece 635 and the reservoir 610 may be operatively engaged when the user connects the reservoir assembly 602 with the base assembly 604.

The covering 640 may be located on the port 612 of the reservoir 610. The covering 640 may be pierceable by the needle 630. The needle 630 may be supported by the mating piece 635 and positioned to pierce the covering 640 and to enter the reservoir 610 when the user connects the reservoir assembly 602 with the base assembly 604. Thus, when the reservoir assembly 602 and the base assembly 604 are connected, a fluid flow path is established between the reservoir assembly 602 and the base assembly 604. The opening 642 in the covering 640 may be closed or blocked by the mating piece 635 when the user connects the reservoir assembly 602 with the base assembly 604, such that, for example, fluidic media can no longer flow out the port 612 into the chamber 650.

In some embodiments of the present invention, the system 600 may further include a structure 655 having the chamber 650. The chamber of the structure 650 may be connected to the port 612 of the reservoir 610. In other embodiments, the chamber 650 may be connectable or otherwise in flow communication with the interior volume 615 of the reservoir 610. For example, fluidic media may be expelled from the interior volume 615 of the reservoir 610 through the opening 642 in the covering 640 into the chamber 650. The chamber 650 may have an interior volume for collecting fluidic media expelled through the opening 642 from the interior volume 615 of the reservoir 610 before the mating piece 635 and the reservoir 610 are connected or otherwise operatively engaged. Fluidic media may be expelled from the interior volume 615 of the reservoir 610 before the mating piece 635 and the reservoir 610 are operatively engaged in a case where a pressure difference exists between the interior volume 615 of the reservoir 610 and the chamber 650. The structure 655 having the chamber 650 may be located outside of the reservoir 610. For example, the chamber 650 may be adjacent to the reservoir 610. In other embodiments of the present invention, such as the embodiment illustrated in FIG. 12C, a structure 656 having a chamber 651 may be located within the reservoir 610.

As shown in FIG. 12A, the port 612 of the reservoir 610 may be initially in an open position, such that fluidic media expelled from the interior volume 615 of the reservoir 610 to equalize pressure within the interior volume 615 of the reservoir 610 can flow freely or bolus through the port 612 and the opening 642 in the covering 640. Fluidic media may flow through the port 612 and the opening 642 in the covering 640 until pressure within the interior volume 615 of the reservoir 610 has been sufficiently equalized with respect to pressure in the chamber 650.

In further embodiments of the present invention, the structure 655 may include a membrane wall 652, which may comprise an elastomeric material, or the like. The membrane wall 652 may be configured to expand (652' in FIG. 11B) outwardly to increase the interior volume of the chamber 650 in a case where the chamber 650 sufficiently fills with fluidic media. The membrane wall 652 may also be configured to allow for pressure equalization across it through the use of a hydrophobic or hydrophilic filter or similar material. In yet further embodiments of the present invention, the structure 655 may have an opening (not shown) for purging fluidic media collected in the interior volume of the chamber 650. This may be useful in a case where the interior volume of the chamber 650 is not sufficiently large enough to contain all of the fluidic media expelled from the interior volume 615 of the reservoir 610.

In some embodiments of the present invention, the reservoir 610 may further include a valve 645, such as, but not limited to, a flapper valve or the like. The flapper valve 645 may be located on the opening 642 of the covering 640. The flapper valve 645 may be forced open when fluidic media is expelled from the interior volume 615 of the reservoir 610 to equalize pressure within the interior volume 615 of the reservoir 610 with respect to pressure in the chamber 650. The flapper valve 645 may be held against the opening 642 by the mating piece 635 when the user connects the reservoir assembly 602 with the base assembly 604, thus closing the opening 642 to prevent fluidic media from flowing out the opening 642 to the chamber 650.

FIG. 12B illustrates a cross-sectional view of the system 600 for equalizing pressure in a second position in accordance with an embodiment of the present invention. Once pressure in the interior volume 615 of the reservoir 610 has been sufficiently equalized, the user may connect the reservoir assembly 602 with the base assembly 604. When the user connects the reservoir assembly 602 with the base assembly 604, the mating piece 635 of the base assembly 604 pushes against the opening 642 of the covering 640 to close or block the opening 642. As a result, fluidic media in the interior volume 615 of the reservoir 610 can no longer flow out the port 612 to the chamber 650. The needle 630 pierces the covering 640 to allow fluidic media contained in the interior volume 615 of the reservoir 610 to flow through the needle 630 to the base assembly 604 and then to the user. For example, fluidic media could flow from the interior volume 615 of the reservoir 610 through the needle 630 into a fluid path (such as 190 in FIG. 7A) in the base assembly 604 and to the user by way of a cannula (such as 194 in FIG. 7A).

The mating piece 635 may securely cover or block the opening 642 to prevent fluidic media from flowing out the opening 642 while the reservoir assembly 602 and the base assembly 604 are connected. In some embodiments of the present invention, the mating piece 635 may close or otherwise seal off the chamber 650, thus inhibiting fluidic media contained in the chamber 650 from flowing back into the interior volume 615 of the reservoir 610 or otherwise flowing out of the chamber 650.

In further embodiments, the needle 630 may be positioned to enter the opening 642 in the covering 640 and to enter the interior volume 615 of the reservoir 610 when the reservoir assembly 602 and the base assembly 604 are connected by the user. In yet further embodiments, the valve 645 may be pierced by the needle 630 when the reservoir assembly 602 and the base assembly 604 are connected by the user. In some embodiments, the needle 630 has a diameter comparable to a diameter of the opening 642 so that the needle 630 seals the opening 642 when the needle 630 enters the opening 642.

Vented Reservoir Embodiments

A fluid reservoir as described in more detail below may include a fluid vent formed therein to accommodate expulsion of pressurized fluidic media from the fluid reservoir. In certain embodiments the fluid vent is implemented as an exposed through hole, wherein the fluid vent is sealed by a sealing arrangement resident on a base assembly (which may be realized as a part of a fluid delivery device, as a part of a fluid transfer assembly used to fill the fluid reservoir, or the like). In contrast to the various embodiments presented above, the fluid vent need not incorporate a self-sealing feature. Rather, the fluid vent can be realized as a simple hole, slot, or other opening formed in the body or neck of the fluid reservoir. This simple configuration relies on one or more sealing elements located at the cooperating base assembly to create a fluid tight seal during delivery of the fluidic media from the fluid reservoir and/or during a filling operation to transfer the fluidic media from a source (such as a vial) to the fluid reservoir.

Figure 14:
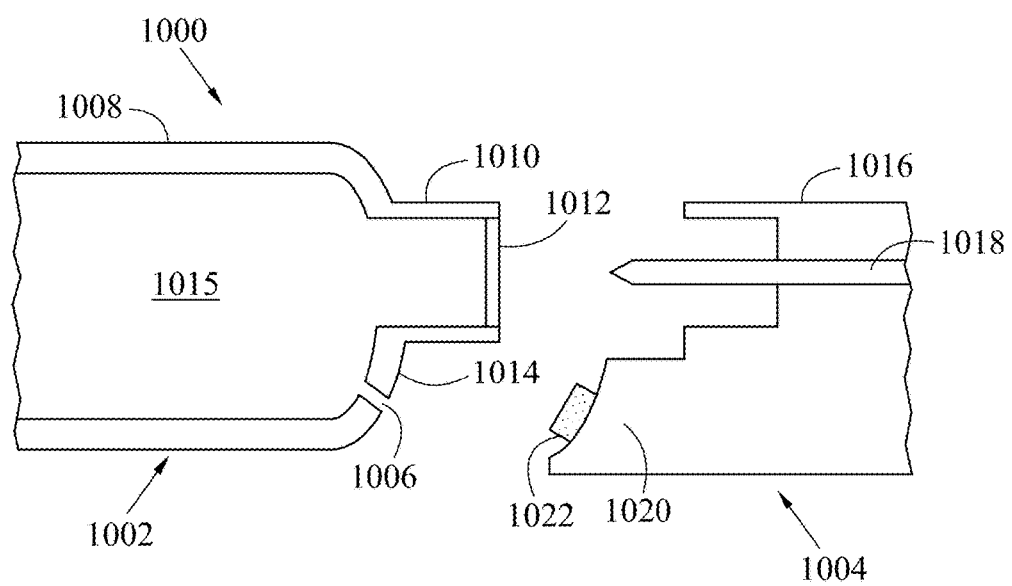
FIG. 14 illustrates a cross-sectional view of a fluid delivery system having a vented fluid reservoir and a base assembly that seals a fluid vent of the reservoir.

FIG. 14 illustrates a cross-sectional view of a fluid delivery system 1000 having a vented fluid reservoir 1002 and a base assembly 1004 that seals a fluid vent 1006 of the fluid reservoir 1002. Some of the basic features and characteristics of the fluid reservoir 1002 and the base assembly 1004 are similar or identical to those described above with reference to various other embodiments, and common features and characteristics will not be redundantly described in detail here.

The fluid reservoir 1002 has a body section 1008 and a neck section 1010 protruding from the body section 1008. The neck section 1010 is covered and sealed with a septum 1012 (as described previously) that can be pierced by a needle to accommodate filling of the fluid reservoir 1002 with fluidic media and/or to accommodate delivery of fluidic media from the fluid reservoir 1002 via a suitably configured fluid delivery system. The fluid vent 1006 may be formed within the body section 1008, the neck section 1010, a shoulder region 1014 of the fluid reservoir 1002, or elsewhere in the fluid reservoir 1002. Moreover, the fluid reservoir 1002 need not include only one fluid vent 1006, and an embodiment of the fluid reservoir 1002 may include any number of fluid vents located in different positions if so desired. The non-limiting and exemplary embodiment depicted in FIG. 14 includes only one fluid vent 1006 formed within the shoulder region 1014 of the fluid reservoir 1002.

The fluid vent 1006 may be realized as a hole, a slot, or any suitably shaped and sized passageway between the interior volume 1015 of the fluid reservoir 1002 and the environment outside the fluid reservoir 1002. In certain embodiments, the fluid vent 1006 is realized as a small through hole (e.g., a round hole having a diameter within the range of about 0.5 mm to about 3.0 mm. The fluid vent 1006 should be large enough to allow pressurized fluidic media to escape, while being small enough to inhibit leaking of the fluidic media under normal operating conditions. In practice, the plunger of the fluid reservoir 1002 will inhibit leakage of the fluidic media after the pressure has been equalized.

As described above with reference to the other embodiments, the base assembly 1004 may include a mating piece 1016 and a needle 1018 that pierces the septum 1012 when the fluid reservoir 1002 and the base assembly 1004 are coupled together. The illustrated embodiment of the base assembly 1004 includes a feature 1020 that supports a sealing arrangement 1022 for the fluid vent 1006. The sealing arrangement 1022 may be realized as one or more compliant or resilient seals that form a fluid tight seal with the fluid vent 1006 when the fluid reservoir 1002 is mated to the base assembly 1004. Although the illustrated embodiment employs a button or pad for the sealing arrangement 1022, other embodiments may utilize a plug that at least partially fits inside the fluid vent 1006, a ring-shaped seal that encircles the fluid vent 1006, or the like. The sealing arrangement 1022 prevents or inhibits expulsion of the fluidic media from the interior volume 1015 when the fluid reservoir 1002 is coupled to the base assembly 1004.

Figure 15:
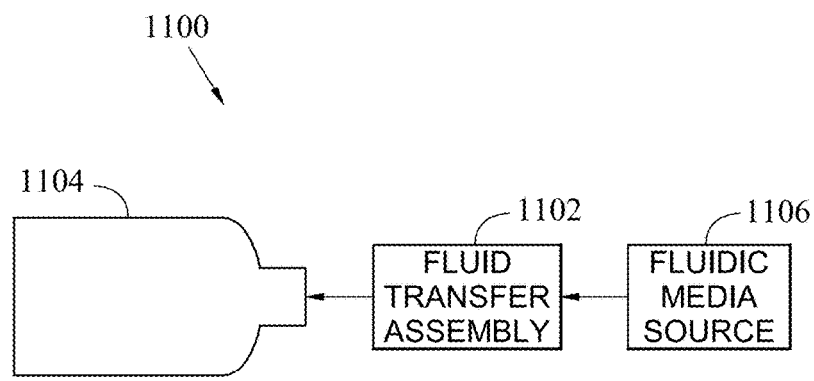
FIG. 15 is a schematic representation of a fluid delivery system during a filling operation.

The base assembly 1004 may form at least a portion of a fluid delivery device for a user, such that the fluidic media can be delivered from the interior volume 1015, through the needle 1018, and to the body of the user via a suitable infusion set. Alternatively (or additionally), the base assembly 1004 may form at least a portion of a fluid transfer assembly that facilitates filling of the fluid reservoir 1002 with the fluidic media. In either implementation, the configuration and functionality of the mating section of the base assembly 1004 and the configuration and functionality of the sealing arrangement 1022 will be as described above. In this regard, FIG. 15 is a schematic representation of a fluid delivery system 1100 during a filling operation. FIG. 15 schematically depicts a fluid transfer assembly 1102 coupled to a fluid reservoir 1104 and to a fluidic media source 1106. It is assumed that the fluid transfer assembly 1102 incorporates or otherwise cooperates with a suitably configured base assembly (e.g., the base assembly 1004 and/or one of the base assembly constructions described below). When the fluid reservoir 1104 is coupled to the fluid transfer assembly 1102, the fluid vent (not shown in FIG. 15) is sealed. This allows fluidic media from the source 1106 to be introduced into the fluid reservoir 1104 via a filling conduit of the fluid transfer assembly 1102. After the fluid reservoir 1104 is filled with the desired amount of the fluidic media, the fluid reservoir 1104 can be separated from the fluid transfer assembly 1102. Removal of the fluid reservoir 1104 from the fluid transfer assembly 1102 unseals the fluid vent of the fluid reservoir 1104, which accommodates expulsion of pressurized fluidic media from the fluid reservoir 1104 (excess pressure may be introduced during the filling operation, as described previously).

Figure 16:
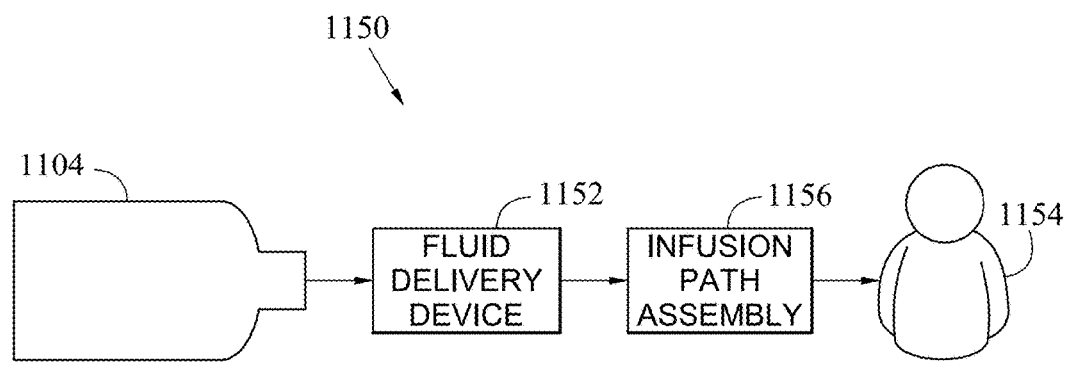
FIG. 16 is a schematic representation of a fluid delivery system during a fluid delivery operation.

After the pressure inside the fluid reservoir 1104 has been equalized, the fluid reservoir 1104 can be coupled to an appropriate fluid delivery apparatus. In this regard, FIG. 16 is a schematic representation of a fluid delivery system 1150 during a fluid delivery operation. This example assumes that the fluid reservoir 1104 is coupled to a fluid delivery device 1152 that cooperates with the fluid reservoir 1104 to deliver the fluidic media to a user 1154 via an infusion path assembly 1156. It is assumed that the fluid delivery device 1152 includes or incorporates a suitably configured base assembly (e.g., the base assembly 1004 and/or one of the base assembly constructions described below). In practice, the base assembly 1004 may be incorporated into the fluid delivery device, into an infusion path assembly, or into any suitable structure. For example, in one particular embodiment, a durable subassembly including the drive system and electronics can be separated from the base assembly, leaving the base assembly affixed to the patient's skin. When the fluid reservoir 1104 is coupled to the fluid delivery device 1152, the fluid vent (not shown in FIG. 16) is sealed. This allows fluidic media from the fluid reservoir 1104 to be provided to the user 1154 via the infusion path assembly 1156 with little to no leakage from the fluid vent.

Figure 17:
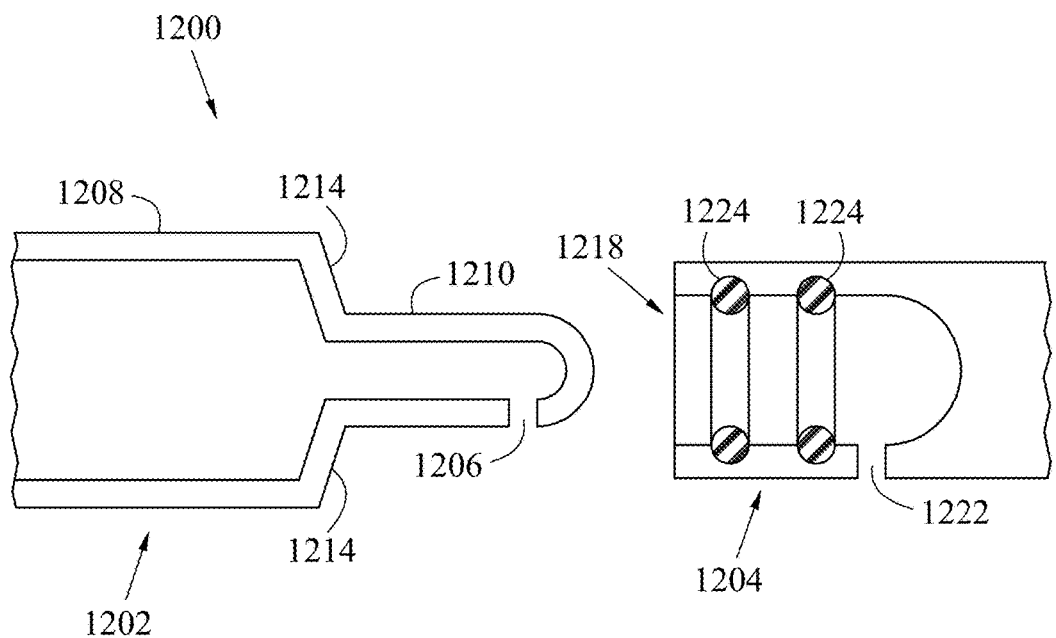
FIG. 17 illustrates a cross-sectional view of a needleless fluid delivery system having a vented fluid reservoir and a base assembly that seals a fluid vent of the reservoir.

FIG. 17 illustrates a cross-sectional view of a needleless fluid delivery system 1200 having a vented fluid reservoir 1202 and a base assembly 1204 that seals a fluid vent 1206 of the fluid reservoir 1202. Unlike the needle-based embodiments described previously, the fluid delivery system 1200 does not rely on a needle to fill the fluid reservoir 1202 with fluidic media and/or to deliver the fluidic media to the user. Instead, the fluid delivery system 1200 uses the fluid vent 1206 to equalize the fluid pressure, to expel the fluidic media during fluid delivery operations, and to receive the fluidic media during filling operations. Thus, the fluid reservoir 1202 and the base assembly 1204 are suitably configured to establish needleless fluid communication when the fluid reservoir 1202 is inserted in the base assembly 1204.

The fluid reservoir 1202 has a body section 1208 and a neck section 1210 protruding from the body section 1208. The fluid vent 1206 may be formed within the body section 1208, the neck section 1210, a shoulder region 1214 of the fluid reservoir 1202, or elsewhere in the fluid reservoir 1202. Moreover, the fluid reservoir 1202 need not include only one fluid vent 1206, and an embodiment of the fluid reservoir 1202 may include any number of fluid vents located in different positions if needed. The non-limiting and exemplary embodiment depicted in FIG. 17 includes only one fluid vent 1206 formed within the neck section 1210 of the fluid reservoir 1202. The fluid vent 1206 may be configured and implemented as described above with reference to FIG. 14. Accordingly, the fluid vent 1206 allows pressurized fluid to escape the fluid reservoir 1202 before the fluid reservoir 1202 is inserted into a fluid delivery apparatus.

The base assembly 1204 includes a sealing receptacle 1218 formed therein. The sealing receptacle 1218 is shaped, sized, and configured as a recess that can receive the neck section 1210 of the fluid reservoir 1202. The base assembly 1204 has a fluid delivery port 1222 formed therein to accommodate transfer of fluidic media (to and/or from the fluid reservoir 1202). As shown in FIG. 17, the fluid delivery port 1222 may be realized as a through hole that communicates with the recess defined by the sealing receptacle 1218. The base assembly 1204 may include a sealing arrangement 1224 located in the sealing receptacle 1218 and configured to form a fluid tight seal with the neck section 1210 of the fluid reservoir 1202. The non-limiting embodiment of the sealing arrangement 1224 shown in FIG. 17 is realized using two seals located within the sealing receptacle 1218. More specifically, the sealing arrangement 1224 is implemented as two o-ring seals positioned around the interior surface of the sealing receptacle 1218 and spaced apart in the major longitudinal dimension of the sealing receptacle 1218.

Figure 18:
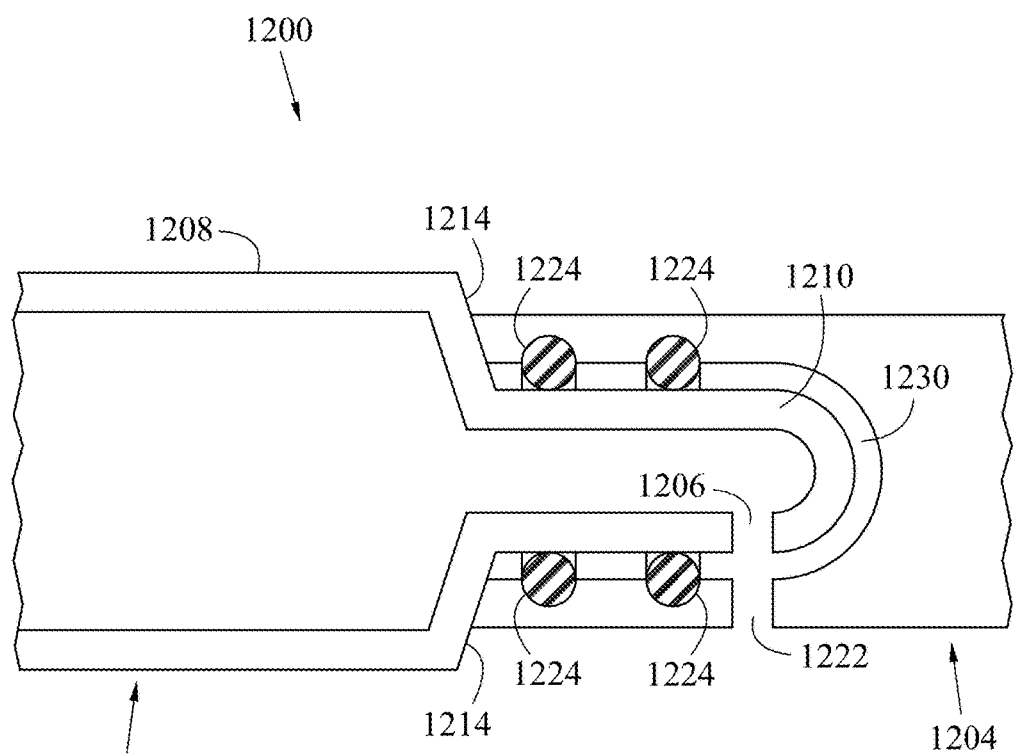
FIG. 18 illustrates a cross-sectional view of the needleless fluid delivery system shown in FIG. 17, with the fluid reservoir coupled to the base assembly.

FIG. 18 illustrates a cross-sectional view of the needleless fluid delivery system 1200 with the fluid reservoir 1202 coupled to the base assembly 1204. When in the inserted state depicted in FIG. 18, the sealing arrangement 1224 forms a fluid tight seal against and around the neck section 1210 of the fluid reservoir 1202, to thereby define and form a chamber 1230 within the sealing receptacle 1218. For this exemplary embodiment, the deepest seal within the recess of the sealing receptacle 1218 serves as one boundary of the chamber 1230. The rest of the chamber 1230 is defined by the space between the outer surface of the neck section 1210 and the inner surface of the recess (i.e., the rounded portion depicted in FIG. 18). Notably, the fluid vent 1206 is located within the chamber 1230 and is in fluid communication with the chamber 1230. Moreover, the fluid delivery port 1222 fluidly communicates with the chamber 1230 when the neck section 1210 is inserted into the sealing receptacle 1218. Although not depicted in FIG. 17 or FIG. 18, the fluid delivery system 1200 may have a suitably configured locking, retaining, or latching mechanism or feature that maintains the fluid reservoir 1202 and the base assembly 1204 in the mated, sealed, and coupled arrangement shown in FIG. 18.

The fluid delivery port 1222 may represent or cooperate with a fluid conduit to accommodate the needleless transfer of fluidic media to and/or from the fluid vent 1206. For example, as described above with reference to FIG. 15, the fluid delivery port 1222 may be in fluid communication with a fluid conduit of a fluid transfer assembly, which can be used to provide fluidic media from a source (e.g., a vial) to the fluid reservoir 1202 during a filling operation. Moreover, as described above with reference to FIG. 16, the fluid delivery port 1222 may be in fluid communication with a fluid conduit of an infusion path assembly, which can be used to provide fluidic media from the fluid reservoir 1202 to the body of the user.

FIG. 19 illustrates a cross-sectional view of another embodiment of a needleless fluid delivery system 1300 having a vented fluid reservoir 1302 and a base assembly 1304 that seals a fluid vent 1306 of the fluid reservoir 1302, and FIG. 20 illustrates a cross-sectional view of the needleless fluid delivery system 1300 with the fluid reservoir 1302 coupled to the base assembly 1304. The fluid delivery system 1300 shares certain features, elements, and characteristics with the fluid delivery system 1200 (see FIG. 17 and FIG. 18), and common aspects of these systems will not be redundantly described here.

The illustrated embodiment of the fluid reservoir 1302 is configured as described above for the fluid reservoir 1202 (see FIG. 17). The base assembly 1304 is similar to that described above for the base assembly 1204 in that it includes a sealing receptacle 1307 that receives the neck section 1310 of the fluid reservoir 1302 to accommodate transfer of the fluidic media through the fluid vent 1306. The base assembly 1304 incorporates a feature that protects the fluid vent 1306 against contamination when the fluid reservoir 1302 is removed from the sealing receptacle 1307.

Referring to FIG. 19, the fluid delivery system 1300 is depicted in its released state, i.e., the fluid reservoir 1302 is released from the base assembly 1304. As shown in FIG. 19, the base assembly 1304 generally includes, without limitation: a main body section 1314; a recess 1316 formed in the body section 1314; a valve cavity 1318 formed in the body section 1314; a valve 1320; a sealing arrangement that includes three seals 1322, 1324, 1326; and a biasing element 1328. The base assembly 1304 also has a fluid delivery port 1330 formed in the body section 1314. Although not shown in FIG. 19 or FIG. 20, the fluid delivery port 1330 may be fluidly coupled to a conduit, a tube, or other fluid passageway or flow path to facilitate transfer of fluidic media to and/or from the fluid delivery port 1330.

The biasing element 1328 may be realized as a spring, a piece of resilient material, a pressurized balloon or pneumatic element, or the like. The biasing element 1328 is located in the valve cavity 1318 between a base 1332 of the valve 1320 and an end wall 1334 of the valve cavity 1318. The biasing element 1328 biases the valve 1320 into an extended position that corresponds to the released state depicted in FIG. 19. Extension of the valve 1320 may be inhibited by a shoulder 1336 (see FIG. 20) or any suitable feature of the base assembly 1304. When the fluid delivery system 1300 is in the released state, the valve 1320 extends forward such that its distal valve end 1338 is exposed to facilitate cleaning or disinfection of the distal valve end 1338 (see FIG. 19). For example, the end of the base assembly 1304, including the distal valve end 1338, can be cleaned with alcohol or any disinfecting agent as so desired.

The recess 1316 receives and accommodates the valve 1320 in the extended position shown in FIG. 19. Moreover, the seals 1322, 1324, 1326 cooperate with and seal against and around the valve 1320 when the valve 1320 is positioned within the recess 1316. The valve 1320 is designed to cooperate with the fluid delivery port 1330 and the seals 1322, 1324, 1326 to inhibit access to the fluid delivery port 1330 when the valve 1320 is extended. As shown in FIG. 19, the seals 1324, 1326 form a fluid tight seal around the fluid delivery port 1330 to protect the fluid delivery port 1330 (and the fluid conduit coupled to the fluid delivery port 1330) against outside contamination. More specifically, the seals 1324, 1326 flank the fluid delivery port 1330, thus isolating the fluid delivery port 1330 and its associated flow path when the fluid reservoir 1302 is removed from the base assembly 1304.

The recess 1316 and the valve cavity 1318 allow the valve 1320 to move between the extended position shown in FIG. 19 (corresponding to the released state) and the retracted position shown in FIG. 20 (corresponding to the inserted state). Thus, the valve cavity 1318 receives most of the valve 1320 when the valve 1320 is in its retracted position. In certain embodiments, at least one seal of the sealing arrangement maintains a fluid tight seal with the valve 1320 during movement of the valve associated with transition between the released and inserted states. For the illustrated embodiment, the deepest seal 1326 maintains contact with the valve 1320 throughout the range of motion of the valve 1320. Accordingly, the seal 1326 can be used to hermetically seal and/or fluidly separate the valve cavity 1318 from the recess 1316.

As depicted in FIG. 20, the recess 1316 also accommodates the neck section 1310 of the fluid reservoir 1302 when the fluid delivery system 1300 is in the inserted state. In the inserted state, the neck section 1310 is received in the sealing receptacle 1307. Notably, insertion of the neck section 1310 displaces the valve 1320 and urges the valve 1320 into its retracted position within the valve cavity 1318. More specifically, the neck section 1310 terminates at a distal neck end 1342 (see FIG. 19), the valve terminates at the distal valve end 1338, and the distal neck end 1342 engages the distal valve end 1338 to maintain the valve 1320 in the retracted position depicted in FIG. 20.

When the neck section 1310 is in the inserted position, the sealing arrangement (e.g., the seals 1322, 1324) forms a fluid tight seal with the outer surface of the neck section 1310. Notably, the seals 1322, 1324 inhibit leakage of fluidic media from the opening of the sealing receptacle 1307, such that the fluidic media can be transferred via the fluid delivery port 1330. As shown in FIG. 20, the fluid vent 1306 fluidly communicates with the fluid delivery port 1330 when the neck region 1310 is coupled within the sealing receptacle 1307. Moreover, the seal 1324 cooperates with the distal valve end 1338 and the outer surface of the neck section 1310 to define a fluid tight chamber 1348 that accommodates the fluidic media; the chamber 1348 is in fluid communication with the fluid vent 1306 and the fluid delivery port 1330. In the inserted state, therefore, the fluid delivery system 1300 functions as described above for the fluid delivery system 1200 (see FIG. 18).

It should be appreciated that the fluid delivery system 1300 may incorporate other types of sealing members, valve configurations, and/or other features to protect the fluid delivery port 1330 when the fluid reservoir 1302 is removed from the base assembly 1304. For example, the fluid delivery system 1300 could employ a flap valve, a retractable plug, a sliding "door" or the like. Moreover, the fluid delivery system 1200 could incorporate a feature to protect the fluid delivery port 1222 without implementing a valve of the type shown in FIG. 19 and FIG. 20.

Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A base assembly for a fluid delivery system comprising a fluid reservoir with a fluid vent for expelling pressurized fluidic media from the fluid reservoir, the base assembly comprising:
   a proximal portion;
   a distal portion formed with a fluid delivery port to accommodate transfer of fluidic media;
   a valve to cooperate with the fluid delivery port;
   a recess to accommodate the fluid reservoir in a first state of the base assembly, and to accommodate the valve in a second state of the base assembly; and
   a sealing arrangement that cooperates with the valve and the fluid reservoir;
   wherein, in the first state, the sealing arrangement cooperates with the fluid reservoir to form a fluid tight chamber in fluid communication with the fluid vent of the fluid reservoir; and
   wherein, in the second state, the sealing arrangement cooperates with the valve to inhibit access to the fluid delivery port.

2. The base assembly of claim 1, wherein, in the first state, the sealing arrangement also cooperates with the valve to form the fluid tight chamber.

3. The base assembly of claim 1, wherein:
   the fluid reservoir terminates at a distal reservoir end;
   the valve terminates at a distal valve end; and
   when the base assembly is in the first state, the distal reservoir end engages the distal valve end to maintain the valve in a retracted position.

4. The base assembly of claim 1, wherein:
   the base assembly forms at least a portion of a fluid delivery device for a user; and
   the fluid delivery device accommodates an infusion path assembly to establish fluid communication with the fluid delivery port to provide the fluidic media from the fluid delivery port to the user.

5. The base assembly of claim 1, wherein:
   the base assembly forms at least a portion of a fluid transfer assembly that facilitates filling of the fluid reservoir with the fluidic media; and
   the fluid transfer assembly comprises a filling conduit for establishing fluid communication with the fluid delivery port to provide the fluidic media to the fluid reservoir.

6. A base assembly for a fluid delivery system comprising a fluid reservoir with a fluid vent for expelling pressurized fluidic media from the fluid reservoir, the base assembly comprising:
   a proximal portion;
   a distal portion formed with a fluid delivery port to accommodate transfer of fluidic media;
   a valve to cooperate with the fluid delivery port;
   a recess to accommodate the fluid reservoir in a first state of the base assembly, and to accommodate the valve in a second state of the base assembly; and
   a sealing arrangement that cooperates with the valve and the fluid reservoir.

7. The base assembly of claim 6 wherein the sealing arrangement forms a fluid tight seal with the valve in a released state, wherein the sealing arrangement includes a first member to form a fluid tight seal with the valve in an inserted state and a second member to form a fluid tight seal with the fluid reservoir in the inserted state;
   wherein, in the inserted state, the fluid vent fluidly communicates with the fluid delivery port in a fluid pathway bound by the first member and the second member; and
   wherein, in the released state, the valve cooperates with the sealing arrangement to inhibit access to the fluid delivery port.

8. The base assembly of claim 7, wherein when in the inserted state, the valve is in a retracted position within the proximal portion of the base assembly.

9. The base assembly of claim 8, wherein, when in the released state, the valve extends such that a distal valve end is exposed to facilitate cleaning or disinfecting of the distal valve end.

10. The base assembly of claim 8, further comprising a biasing element located in the proximal portion of the base assembly to bias the valve into an extended position corresponding to the released state.

11. The base assembly of claim 7, wherein:
    the proximal portion of the base assembly further comprises a valve cavity to receive the valve when the valve is in a retracted position corresponding to the inserted state; and
    the first member forms a fluid tight seal with the valve, when in the inserted state, to fluidly separate the valve cavity from the recess and to prevent fluid flow into the proximal portion of the base assembly.

12. The base assembly of claim 11, wherein the first member maintains the fluid tight seal with the valve during movement of the valve associated with transition between the released state and the inserted state.

13. The base assembly of claim 7, wherein:
    the base assembly forms at least a portion of a fluid delivery device for a user; and
    the fluid delivery system further comprises an infusion path assembly to establish fluid communication with the fluid delivery port to provide the fluidic media from the fluid delivery port to the user.

14. The base assembly of claim 7, wherein:
    the base assembly forms at least a portion of a fluid transfer assembly that facilitates filling of the fluid reservoir with the fluidic media; and
    the fluid transfer assembly comprises a filling conduit for establishing fluid communication with the fluid delivery port to provide the fluidic media to the fluid reservoir.

15. The base assembly of claim 14, wherein the fluid transfer assembly receives a fluidic media source to accommodate transfer of fluidic media from the fluidic media source to the fluid reservoir.

16. The base assembly of claim 7, wherein the fluid reservoir and the base assembly establish needleless fluid communication between the fluid vent and the fluid delivery port in the inserted state.

17. A base assembly for a fluid delivery system comprising a fluid reservoir with a fluid vent for expelling pressurized fluidic media from the fluid reservoir, the base assembly comprising:
- a proximal portion;
- a distal portion;
- an intermediate portion between the proximal portion and the distal portion;
- a fluid delivery port in the intermediate portion;
- a valve movable between an extended position and a retracted position, wherein the valve is located in the proximal portion, the intermediate portion, and the distal portion when in the extended position, and wherein the valve is removed from the intermediate portion and distal portion when in the retracted position;
- a recess to accommodate the fluid reservoir in a first state of the base assembly, and to accommodate the valve in a second state of the base assembly; and
- a sealing arrangement that cooperates with the valve and the fluid reservoir.

18. The base assembly of claim 17 further comprising a recess to accommodate the fluid reservoir in an inserted state during which the fluid reservoir is received in the distal portion and the intermediate portion.

19. The base assembly of claim 18 further comprising a proximal sealing member at a proximal interface between the proximal portion and the intermediate portion to form a fluid tight seal with the valve.

20. The base assembly of claim 18 further comprising a distal sealing member at a distal interface between the intermediate portion and the distal portion to form a fluid tight seal with the fluid reservoir in the inserted state and to form a fluid tight seal with the valve in the extended position, wherein, in the inserted state, fluid communication is opened between the fluid vent and the fluid delivery port within the intermediate portion.

* * * * *